(12) United States Patent
Inoue et al.

(10) Patent No.: US 9,412,953 B2
(45) Date of Patent: Aug. 9, 2016

(54) LIGHT-EMITTING ELEMENT, LIGHT-EMITTING DEVICE, ELECTRONIC DEVICE, LIGHTING DEVICE, AND HETEROCYCLIC COMPOUND

(71) Applicant: Semiconductor Energy Laboratory Co., Ltd., Kanagawa-ken (JP)

(72) Inventors: Hideko Inoue, Kanagawa (JP); Miyako Morikubo, Kanagawa (JP); Naoaki Hashimoto, Kanagawa (JP); Hiromi Seo, Kanagawa (JP); Satoshi Seo, Kanagawa (JP); Miki Kanamoto, Kanagawa (JP); Tomoka Nakagawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 405 days.

(21) Appl. No.: 13/958,072

(22) Filed: Aug. 2, 2013

(65) Prior Publication Data

US 2014/0034931 A1 Feb. 6, 2014

(30) Foreign Application Priority Data

Aug. 3, 2012 (JP) ................................. 2012-172801

(51) Int. Cl.
*H01L 51/50* (2006.01)
*H01L 51/00* (2006.01)

(52) U.S. Cl.
CPC ........ *H01L 51/0067* (2013.01); *H01L 51/0074* (2013.01); *H01L 51/006* (2013.01); *H01L 51/0052* (2013.01); *H01L 51/0059* (2013.01);
(Continued)

(58) Field of Classification Search
None
See application file for complete search history.

(56) References Cited

U.S. PATENT DOCUMENTS 6,821,646 B2 11/2004 Tsuboyama et al.
6,838,818 B2 1/2005 Furugori et al.
(Continued)

FOREIGN PATENT DOCUMENTS

EP 2 468 731 A1 6/2012
JP 2002-324677 11/2002
(Continued)

OTHER PUBLICATIONS

Goldsmith, C.R. et al., "C—H Bond Activation by a Ferric Methoxide Complex: Modeling the Rate-Determining Step in the Mechanism of Lipoxygenase," Journal of the American Chemical Society, vol. 124, No. 1, 2002, pp. 83-96.
(Continued)

*Primary Examiner* — Gregory Clark
(74) *Attorney, Agent, or Firm* — Husch Blackwell LLP

(57) ABSTRACT

A light-emitting element with high heat resistance and high emission efficiency is provided. A novel heterocyclic compound that can be used in such a light-emitting element is provided. One embodiment of the present invention is a light-emitting element which includes, between a pair of electrodes, a layer containing a first organic compound, a second organic compound, and a light-emitting substance; the first organic compound includes one pyrimidine ring and one ring with a hole-transport skeleton; the second organic compound is an aromatic amine; and the light-emitting substance converts triplet excitation energy into light. A combination of the first organic compound, which includes the one pyrimidine ring and the one ring with the hole-transport skeleton, and the second organic compound, which is the aromatic amine, forms an exciplex.

16 Claims, 23 Drawing Sheets

(52) U.S. Cl.
CPC ......... *H01L 51/0072* (2013.01); *H01L 51/0085* (2013.01); *H01L 51/5016* (2013.01); *H01L 51/5024* (2013.01); *H01L 51/5072* (2013.01)

(56) References Cited

U.S. PATENT DOCUMENTS

| | | | |
|---|---|---|---|
| 7,166,958 B2 | 1/2007 | Furugori et al. | |
| 7,332,233 B2 | 2/2008 | Park et al. | |
| 7,446,471 B2 | 11/2008 | Furugori et al. | |
| 7,649,077 B2 | 1/2010 | Craig et al. | |
| 7,651,791 B2 | 1/2010 | Nakano et al. | |
| 7,736,758 B2 | 6/2010 | Furugori et al. | |
| 7,790,299 B2 | 9/2010 | Furugori et al. | |
| 7,846,560 B2 | 12/2010 | Nakano et al. | |
| 7,910,227 B2 | 3/2011 | Furugori et al. | |
| 8,012,602 B2 | 9/2011 | Schafer et al. | |
| 8,128,727 B2 | 3/2012 | Nomura et al. | |
| 8,142,911 B2 | 3/2012 | Kadoma et al. | |
| 2002/0063516 A1 | 5/2002 | Tsuboyama et al. | |
| 2005/0048310 A1 | 3/2005 | Cocchi et al. | |
| 2006/0008670 A1 | 1/2006 | Lin et al. | |
| 2006/0134464 A1 | 6/2006 | Nariyuki | |
| 2006/0228577 A1 | 10/2006 | Nagara | |
| 2007/0141387 A1 | 6/2007 | Nakano et al. | |
| 2007/0190355 A1 | 8/2007 | Ikeda et al. | |
| 2008/0160345 A1 | 7/2008 | Inoue et al. | |
| 2008/0286604 A1 | 11/2008 | Inoue et al. | |
| 2010/0019203 A1 | 1/2010 | Akino et al. | |
| 2010/0052527 A1 | 3/2010 | Ikeda et al. | |
| 2010/0084971 A1 | 4/2010 | Nakano et al. | |
| 2010/0240892 A1 | 9/2010 | Schafer et al. | |
| 2011/0089821 A1 | 4/2011 | Furugori et al. | |
| 2012/0098417 A1 | 4/2012 | Inoue et al. | |
| 2012/0126208 A1* | 5/2012 | Kawamura | H01L 51/0067 257/40 |
| 2012/0126217 A1 | 5/2012 | Yoshida et al. | |
| 2012/0133273 A1 | 5/2012 | Inoue et al. | |
| 2012/0205632 A1 | 8/2012 | Shitagaki et al. | |
| 2012/0205687 A1 | 8/2012 | Yamazaki et al. | |
| 2012/0214993 A1 | 8/2012 | Aihara et al. | |
| 2012/0242219 A1 | 9/2012 | Seo et al. | |
| 2012/0248421 A1 | 10/2012 | Yamazaki et al. | |
| 2012/0248427 A1 | 10/2012 | Nishiura et al. | |
| 2012/0256535 A1 | 10/2012 | Seo et al. | |
| 2012/0274201 A1 | 11/2012 | Seo et al. | |
| 2012/0277427 A1 | 11/2012 | Inoue et al. | |
| 2013/0048964 A1 | 2/2013 | Takeda et al. | |

FOREIGN PATENT DOCUMENTS

| | | |
|---|---|---|
| JP | 2003-45662 | 2/2003 |
| JP | 2005-53912 | 3/2005 |
| JP | 2007-123392 | 5/2007 |
| JP | 2009-158848 | 7/2009 |
| JP | 2011-121877 | 6/2011 |
| JP | 2011-219442 | 11/2011 |
| JP | 2011-219443 | 11/2011 |
| WO | WO 2008/096735 A1 | 8/2008 |
| WO | WO 2011/046182 A1 | 4/2011 |
| WO | WO 2011/070992 A1 | 6/2011 |
| WO | WO 2011/149240 A2 | 12/2011 |
| WO | WO 2012/096263 A1 | 7/2012 |

OTHER PUBLICATIONS

Onishi, T. et al, "A Method of Measuring an Energy Level," *High Molecular EL Materials—Development of Light-Emitting High Molecular Compounds*, Kyoritsu Shuppan, Dec. 25, 2004, pp. 64-67 (with English translation, pp. 1-3).

Achelle, S. et al., "Star-and Banana-Shaped Oligomers with a Pyrimidine Core: Synthesis and Light-Emitting Properties," European Journal of Organic Chemistry, 2008, pp. 3129-3140.

Su, S.-J. et al., "RGB Phosphorescent Organic Light-Emitting Diodes by Using Host Materials with Heterocyclic Cores: Effect of Nitrogen Atom Orientations," Chemistry of Materials, vol. 23, No. 2, 2011, pp. 274-284.

Seo, J.H., et al., "Efficient Blue-Green Organic Light-Emitting Diodes Based on Heteroleptic tris-Cyclometalated Iridium(III) Complexes," Thin Solid Films, vol. 517, No. 5, 2009, pp. 1807-1810.

* cited by examiner

LIGHT-EMITTING ELEMENT, LIGHT-EMITTING DEVICE, ELECTRONIC DEVICE, LIGHTING DEVICE, AND HETEROCYCLIC COMPOUND

BACKGROUND OF THE INVENTION

1. Field of the Invention

The present invention relates to a light-emitting element, a light-emitting device, an electronic device, a lighting device, and a heterocyclic compound.

2. Description of the Related Art

In recent years, research and development have been extensively conducted on light-emitting elements using electroluminescence (EL). In a basic structure of such a light-emitting element, a layer containing a light-emitting substance is interposed between a pair of electrodes. By voltage application to this element, light emission can be obtained from the light-emitting substance.

Such a light-emitting element is a self-luminous element and has advantages over liquid crystal displays, such as high visibility of pixels and no need of a backlight; thus, such a light-emitting element is thought to be suitable as a flat panel display element. Besides, such a light-emitting element has advantages in that it can be manufactured to be thin and lightweight, and has very fast response speed.

Furthermore, since such a light-emitting element can be formed in a film form, the light-emitting element makes it possible to provide planar light emission; thus, a large-area element utilizing planar light emission can be easily formed. This feature is difficult to obtain with point light sources typified by incandescent lamps and LEDs or linear light sources typified by fluorescent lamps. Thus, the light-emitting element also has great potential as a planar light source applicable to lighting and the like.

Such light-emitting elements utilizing electroluminescence can be broadly classified according to whether a light-emitting substance is an organic compound or an inorganic compound. In the case of an organic EL element in which a layer containing an organic compound used as a light-emitting substance is provided between a pair of electrodes, application of voltage to the light-emitting element causes injection of electrons from a cathode and holes from an anode into the layer containing the organic compound having a light-emitting property and thus current flows. The injected electrons and holes then lead the organic compound having a light-emitting property to its excited state, so that light emission is obtained from the excited organic compound having a light-emitting property.

The excited state formed by an organic compound can be a singlet excited state or a triplet excited state. Light emission from the singlet excited state (S*) is called fluorescence, and light emission from the triplet excited state (T*) is called phosphorescence. Further, the statistical generation ratio of S* to T* in a light-emitting element is thought to be 1:3.

With a compound that can convert a singlet excited state into light (hereinafter, called a fluorescent compound), only light emission from the singlet excited state (fluorescence) is observed and that from the triplet excited state (phosphorescence) is not observed, at room temperature. Accordingly, the internal quantum efficiency (the ratio of the number of generated photons to the number of injected carriers) of a light-emitting element including the fluorescent compound is assumed to have a theoretical limit of 25%, on the basis of S*:T*=1:3.

In contrast, an observation on a compound that can convert a triplet excited state into light (hereinafter, called a phosphorescent compound) shows light emission from the triplet excited state (phosphorescence). Further, since intersystem crossing (i.e., transition from a singlet excited state to a triplet excited state) easily occurs in a phosphorescent compound, the internal quantum efficiency can be theoretically increased to 75% to 100%. In other words, the emission efficiency can be three to four times as much as that of a fluorescent compound. For this reason, light-emitting elements using phosphorescent compounds have been under active development recently in order that highly efficient light-emitting elements can be obtained.

When formed using the above-described phosphorescent compound, a light-emitting layer of a light-emitting element is often formed such that the phosphorescent compound is dispersed in a matrix containing another compound in order to suppress concentration quenching or quenching due to triplet-triplet annihilation in the phosphorescent compound. Here, the compound as the matrix is called a host material, and the compound dispersed in the matrix, such as a phosphorescent compound, is called a guest material.

In the case where a phosphorescent compound is a guest material, a host material needs to have higher triplet excitation energy (energy difference between a ground state and a triplet excited state) than the phosphorescent compound.

Furthermore, since singlet excitation energy (energy difference between a ground state and a singlet excited state) is higher than triplet excitation energy, a substance that has high triplet excitation energy also has high singlet excitation energy. Thus, the above substance that has high triplet excitation energy is also effective in a light-emitting element using a fluorescent compound as a light-emitting substance.

A compound including pyrimidine or the like has been studied as an electron-transport material or as a host material in the case where a phosphorescent compound is used as a guest material (e.g., Patent Document 1).

A compound in which a carbazole skeleton and a nitrogen-containing hetero aromatic ring are combined is disclosed as an example of a host material in the case where a phosphorescent compound is used as a guest material (e.g., Patent Document 2).

REFERENCE

[Patent Document 1] Japanese Published Patent Application No. 2003-45662

[Patent Document 2] PCT International Publication No. 2011-046182

SUMMARY OF THE INVENTION

As disclosed in Patent Document 1 or Patent Document 2, a host material for a phosphorescent compound or a guest material of a phosphorescent compound has been actively developed. However, a light-emitting element still needs to be improved in terms of emission efficiency, reliability, emission characteristics, synthesis efficiency, and cost, and a light-emitting element with better characteristics is expected to be developed.

In view of the above, in one embodiment of the present invention, a light-emitting element which has high heat resistance, low drive voltage, and a long lifetime is provided. Further, in one embodiment of the present invention, a light-emitting element with high heat resistance and high emission efficiency is provided. In one embodiment of the present invention, a novel heterocyclic compound is provided. By application of this novel heterocyclic compound, a light-emitting element with a long lifetime and a light-emitting element with a long lifetime and high emission efficiency are provided. In one embodiment of the present invention, a light-emitting device, an electronic device, and a lighting device each using the light-emitting element are provided.

Embodiments of the present invention are synthesis of a novel heterocyclic compound with high heat resistance and a light-emitting element with a long lifetime which uses the obtained novel heterocyclic compound. Another embodiment of the present invention is a light-emitting element which includes a light-emitting layer containing a first organic compound that is the above novel heterocyclic compound, a second organic compound that is another material, and a light-emitting substance converting triplet excitation energy into light. A combination of the first organic compound and the second organic compound allows generation of an exciplex (an excited complex), and with the use of energy from the exciplex, the light-emitting substance converting triplet excitation energy into light emits light. Note that a difference between an $S_1$ level and a $T_1$ level of the generated exciplex is extremely small as compared to a difference between an $S_1$ level and a $T_1$ level of each of the substances (first organic compound and second organic compound) before exciplex formation. Thus, an emission spectrum of the exciplex can largely overlap with an absorption spectrum of the light-emitting substance converting triplet excitation energy into light, and thus efficiency of energy transfer from a $T_1$ level of the exciplex to the light-emitting substance converting triplet excitation energy into light can be increased, which leads to an increase in emission efficiency of a light-emitting element.

That is, one embodiment of the present invention is a light-emitting element which includes, between a pair of electrodes, a layer containing a first organic compound, a second organic compound, and a light-emitting substance; the first organic compound includes one pyrimidine ring and one ring with a hole-transport skeleton; the second organic compound is an aromatic amine; and the light-emitting substance converts triplet excitation energy into light. A combination of the first organic compound, which includes the one pyrimidine ring and the one ring with the hole-transport skeleton, and the second organic compound, which is the aromatic amine, forms an exciplex.

Another embodiment of the present invention is a light-emitting element which includes, between a pair of electrodes, a layer containing a first organic compound, a second organic compound, and a light-emitting substance; the first organic compound includes one pyrimidine ring and one ring with a hole-transport skeleton, and has a molecular weight greater than or equal to 400 and less than or equal to 1200; the second organic compound is an aromatic amine; and the light-emitting substance converts triplet excitation energy into light. A combination of the first organic compound, which includes the one pyrimidine ring and the one ring with the hole-transport skeleton and has a molecular weight greater than or equal to 400 and less than or equal to 1200, and the second organic compound, which is the aromatic amine, forms an exciplex.

In any of the above structures, as the ring with the hole-transport skeleton included in the first organic compound, a carbazole ring, a dibenzothiophene ring, and a dibenzofuran ring can be given.

In any of the above structures, the first organic compound has a high electron-transport property and thus can be used for an electron-transport layer, an electron-injection layer, or a light-emitting layer.

In any of the above structures, the ring with the hole-transport skeleton is a carbazole ring, a dibenzothiophene ring, or a dibenzofuran ring.

A further embodiment of the present invention is a heterocyclic compound represented by General Formula (G1). Note that the heterocyclic compound represented by General Formula (G1) can be used as the first organic compound in any of the above structures.

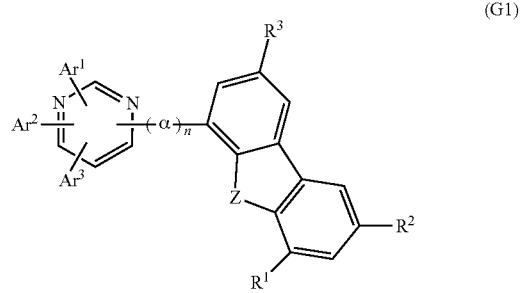

Note that in the formula, $Ar^1$ to $Ar^3$ separately represent any of hydrogen, an alkyl group having 1 to 4 carbon atoms, a substituted or unsubstituted phenyl group, and a substituted or unsubstituted biphenyl group, and $R^1$ to $R^3$ separately represent any of hydrogen, an alkyl group having 1 to 4 carbon atoms, and a substituted or unsubstituted aryl group having 6 to 13 carbon atoms. α represents a substituted or unsubstituted phenylene group and n is 2 or 3. Z represents oxygen or sulfur.

In the above structure, the phenylene group represented by α is an o-phenylene group, a m-phenylene group, or a p-phenylene group.

A still further embodiment of the present invention is a heterocyclic compound represented by General Formula (G2). Note that the heterocyclic compound represented by General Formula (G2) can be used as the first organic compound in any of the above structures.

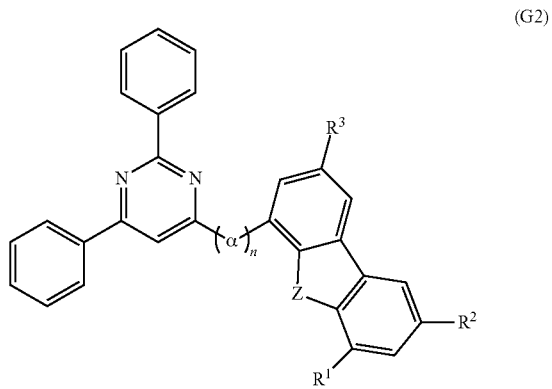

Note that in the formula, $R^1$ to $R^3$ separately represent any of hydrogen, an alkyl group having 1 to 4 carbon atoms, and a substituted or unsubstituted aryl group having 6 to 13 carbon atoms. α represents a substituted or unsubstituted phenylene group and n is 2 or 3. Z represents oxygen or sulfur.

A yet still further embodiment of the present invention is a heterocyclic compound represented by Structural Formula (100). Note that the heterocyclic compound represented by Structural Formula (100) is included in the categories of the structures represented by General Formula (G1) and General Formula (G2).

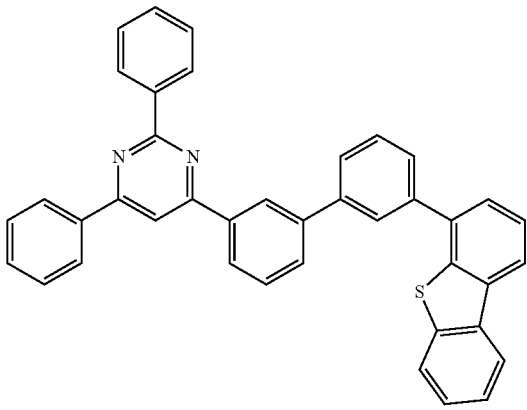

(100)

A yet still further embodiment of the present invention is a heterocyclic compound represented by Structural Formula (101). Note that the heterocyclic compound represented by Structural Formula (101) is included in the categories of the structures represented by General Formula (G1) and General Formula (G2).

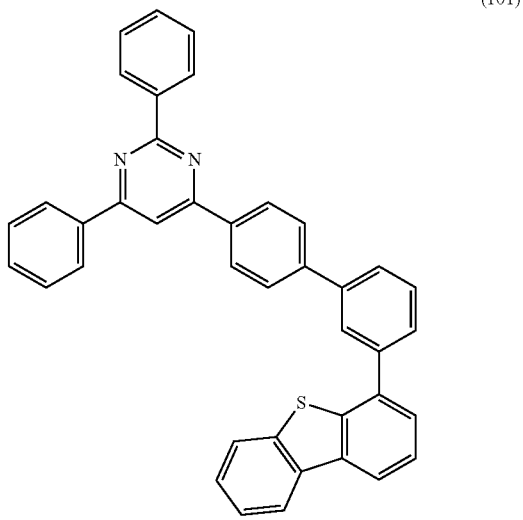

(101)

Since the heterocyclic compounds of embodiments of the present invention which are represented by General Formulae (G1) and (G2) have high heat resistance, by using any of these materials in a light-emitting element, the light-emitting element can have a long lifetime.

Further, the present invention includes, in its scope, electronic devices and lighting devices including light-emitting devices, as well as light-emitting devices including light-emitting elements. The light-emitting device in this specification refers to an image display device and a light source (e.g., a lighting device). In addition, the light-emitting device includes, in its category, all of a module in which a light-emitting device is connected to a connector such as a flexible printed circuit (FPC) or a tape carrier package (TCP), a module in which a printed wiring board is provided on the tip of a TCP, and a module in which an integrated circuit (IC) is directly mounted on a light-emitting element by a chip on glass (COG) method.

In one embodiment of the present invention, a light-emitting element which has high heat resistance, low drive voltage, and a long lifetime can be provided. Further, in one embodiment of the present invention, a light-emitting element with high heat resistance and high emission efficiency can be provided. In one embodiment of the present invention, a novel heterocyclic compound can be provided. Note that by application of the novel heterocyclic compound, a light-emitting element with high heat resistance and a long lifetime can be provided. In addition, by application of the novel heterocyclic compound, a light-emitting element with a long lifetime and high emission efficiency can also be provided. Furthermore, in one embodiment of the present invention, a light-emitting device, an electronic device, and a lighting device in which power consumption is reduced with the use of the light-emitting element can be provided.

DETAILED DESCRIPTION OF THE INVENTION

Figure 1:
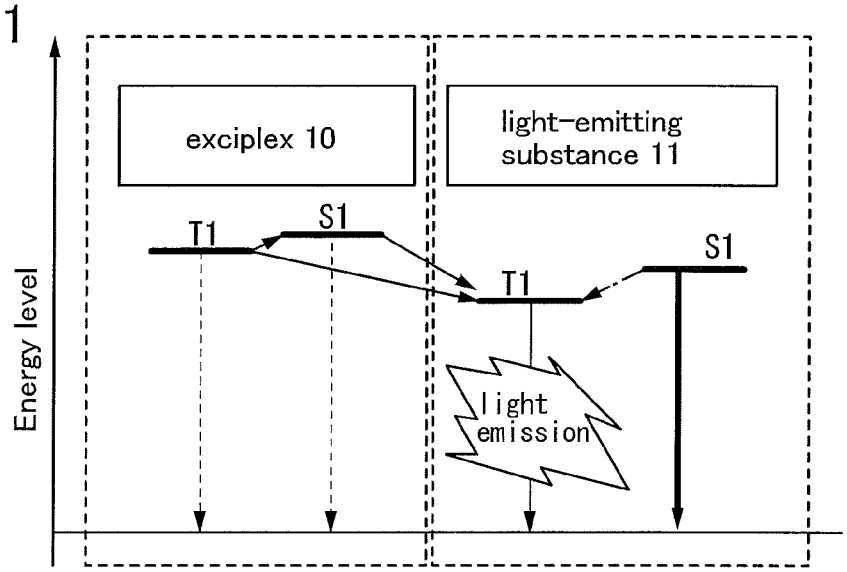
FIG. 1 shows a concept of one embodiment of the present invention.

Hereinafter, embodiments of the present invention will be described with reference to the drawings. Note that the present invention is not limited to the following description, and modes and details thereof can be modified in various ways without departing from the spirit and scope of the invention. Thus, the present invention should not be construed as being limited to the description in the following embodiments.

(Embodiment 1)

In this embodiment, heterocyclic compounds each of which is one embodiment of the present invention will be described.

The heterocyclic compound that is one embodiment of the present invention includes one pyrimidine ring and one ring with a hole-transport skeleton. Note that the heterocyclic compound in this embodiment which includes one pyrimidine ring and one ring with a hole-transport skeleton has a structure represented by General Formula (G1).

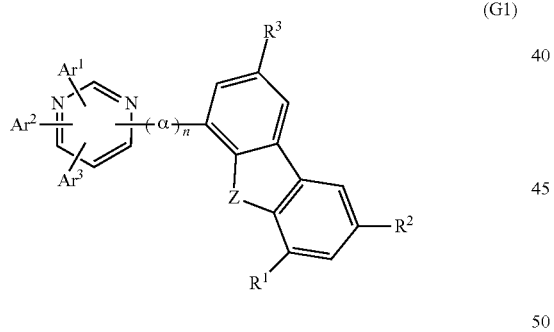

(G1)

In General Formula (G1), $Ar^1$ to $Ar^3$ separately represent any of hydrogen, an alkyl group having 1 to 4 carbon atoms, a substituted or unsubstituted phenyl group, and a substituted or unsubstituted biphenyl group, and $R^1$ to $R^3$ separately represent any of hydrogen, an alkyl group having 1 to 4 carbon atoms, and a substituted or unsubstituted aryl group having 6 to 13 carbon atoms. α represents a substituted or unsubstituted phenylene group and n is 2 or 3. Z represents oxygen or sulfur. Note that the phenylene group represented by α is an o-phenylene group, a m-phenylene group, or a p-phenylene group.

Note that the heterocyclic compound that is one embodiment of the present invention preferably has a structure represented by General Formula (G2) where two of $Ar^1$ to $Ar^3$ in General Formula (G1) represent phenyl groups and the other represents hydrogen, in which case synthesis can be facilitated.

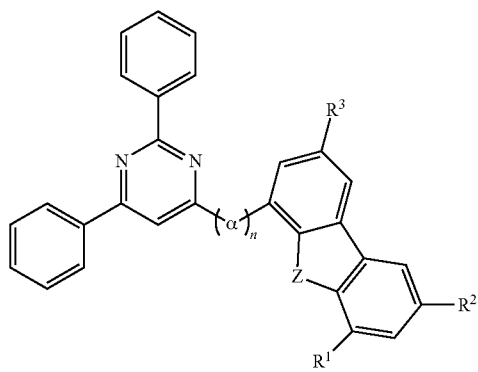

(G2)

Note that in General Formula (G2), $R^1$ to $R^3$ separately represent any of hydrogen, an alkyl group having 1 to 4 carbon atoms, and a substituted or unsubstituted aryl group having 6 to 13 carbon atoms. α represents a substituted or unsubstituted phenylene group and n is 2 or 3. Z represents oxygen or sulfur.

As specific structures of $(α)_n$ (where n is 2 or 3) in General Formula (G1) or (G2), there are substituents represented by Structural Formulae (1-1) to (1-4), for example.

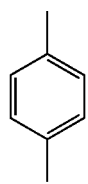

(1-1)

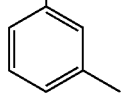

(1-2)

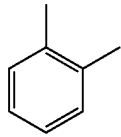

(1-3)

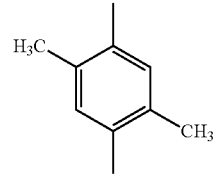

(1-4)

As specific structures of $Ar^1$ to $Ar^3$ and $R^1$ to $R^3$ in General Formula (G1) or (G2), there are substituents represented by Structural Formulae (2-1) to (2-19), for example.

(2-1)

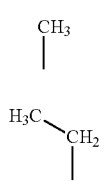 (2-2)
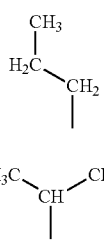 (2-3)
(2-4)
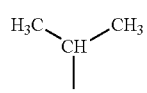 (2-5)
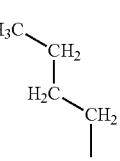 (2-6)
(2-7)
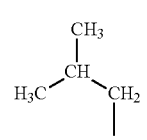 (2-8)
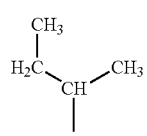 (2-9)
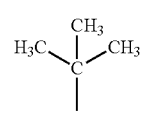 (2-10)
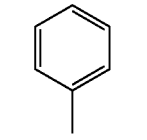 (2-11)
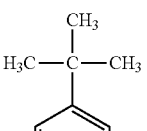
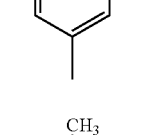 (2-12)
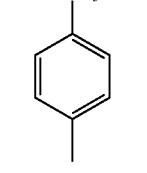
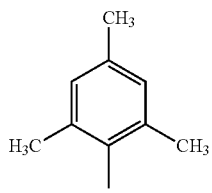 (2-13)
(2-14)
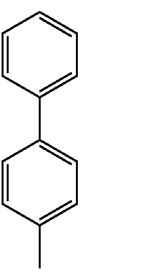
(2-15)
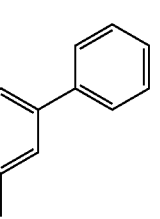
(2-16)
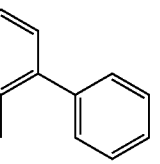
(2-17)
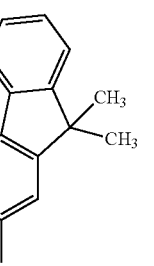
(2-18)
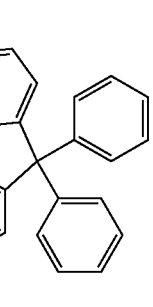

(2-19)
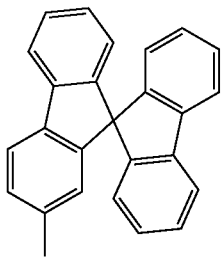
As specific examples of the heterocyclic compound that can be used for one embodiment of the present invention, there are heterocyclic compounds represented by Structural Formulae (100) to (120). However, it is to be noted that the present invention is not limited to these.
(100)
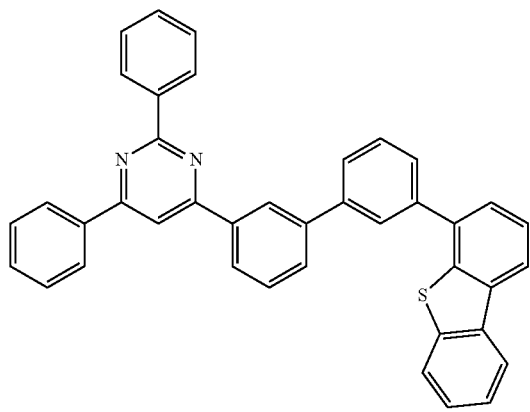
(101)
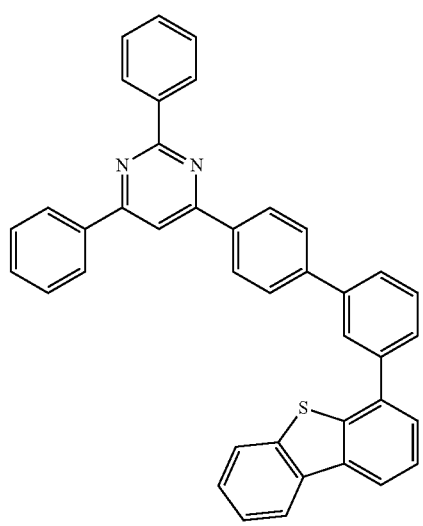
(102)
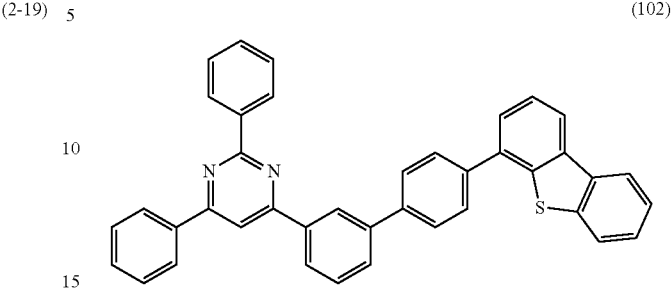
(103)
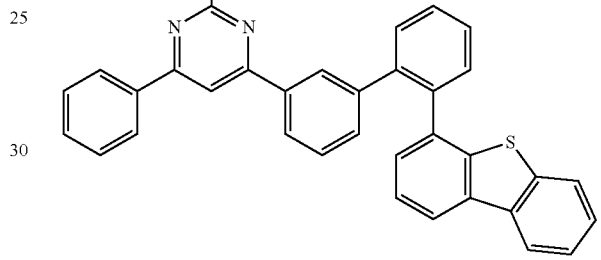
(104)
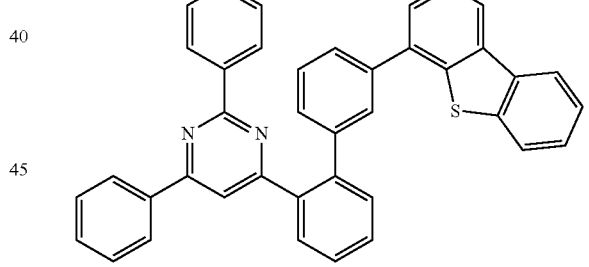
(105)
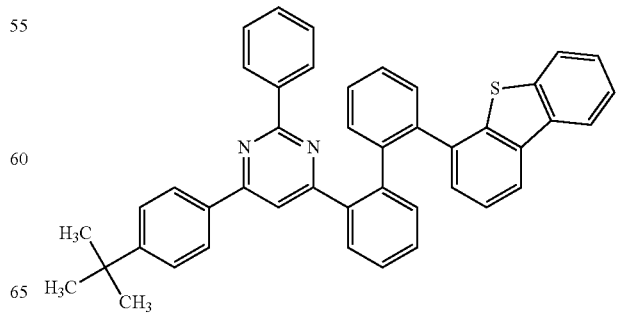

(106)
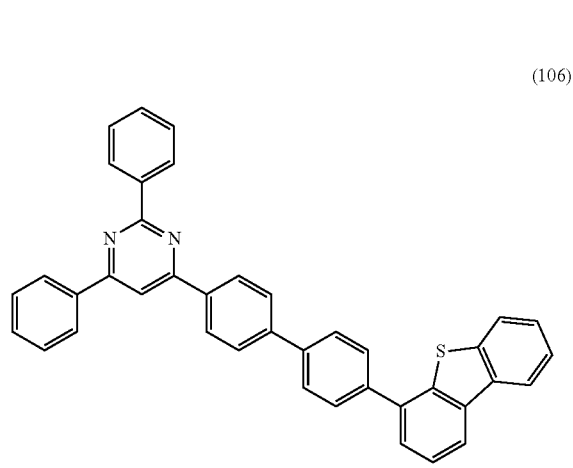
(109)
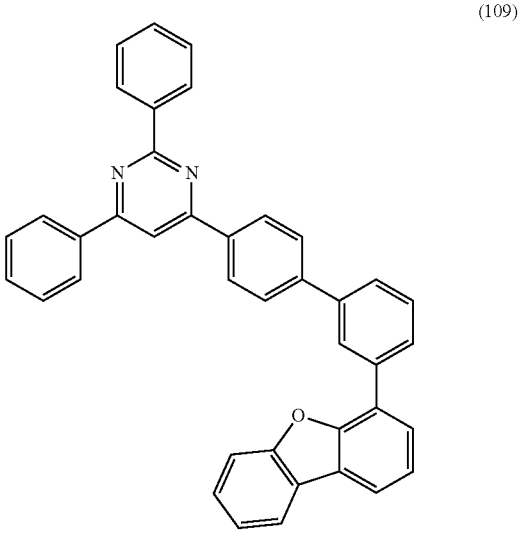
(107)
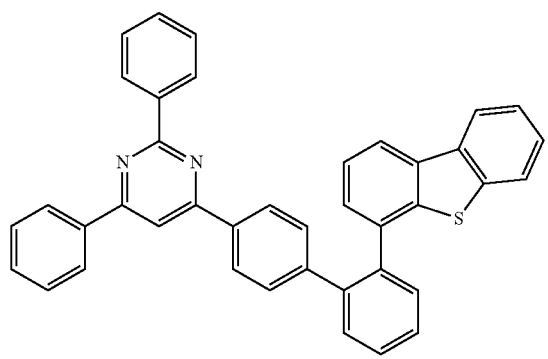
(110)
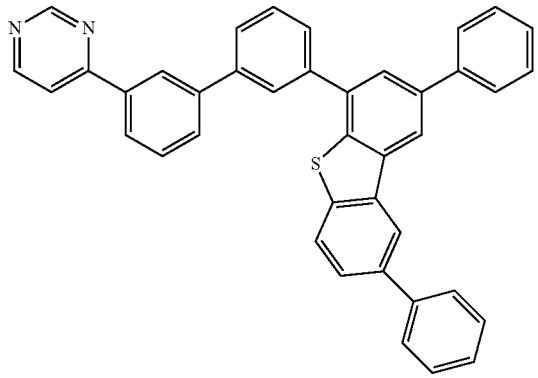
(108)
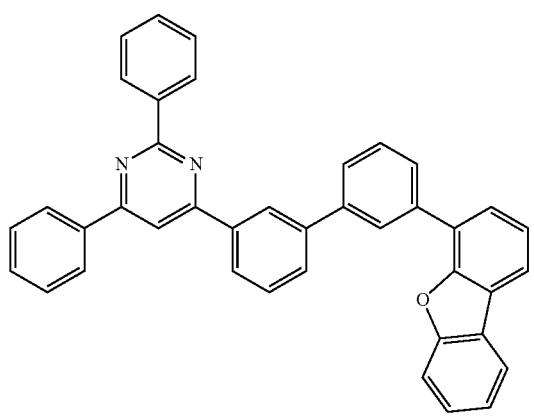
(111)
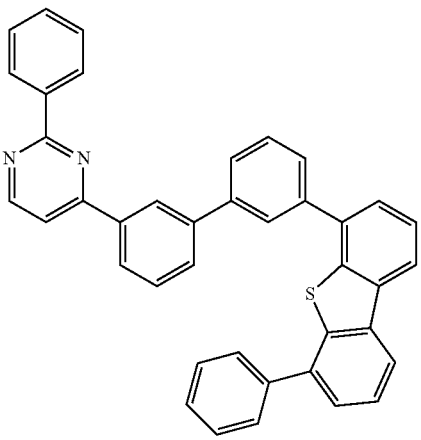

(112)
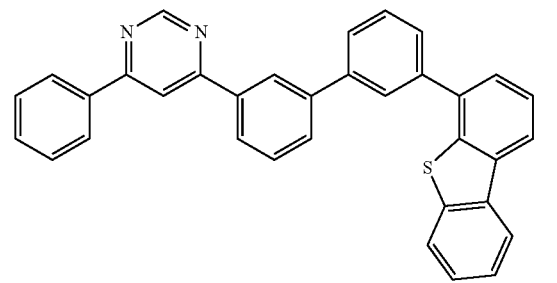
(113)
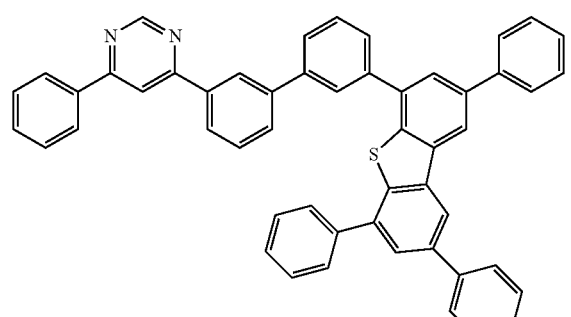
(114)
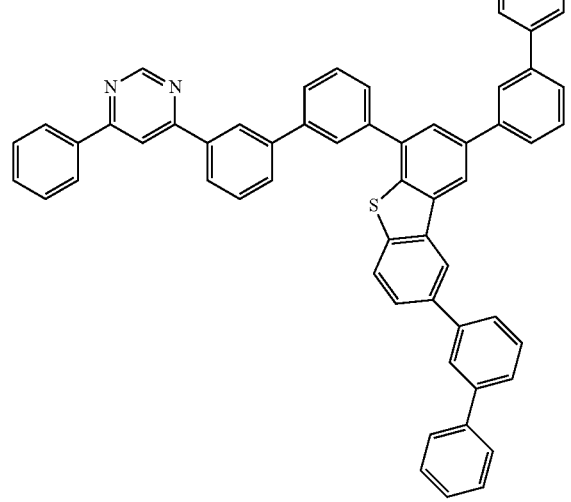
(115)
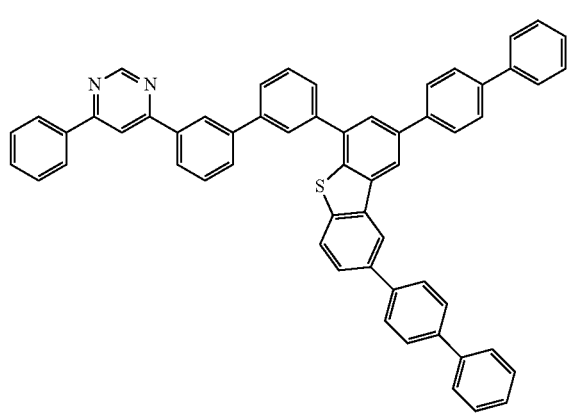
(116)
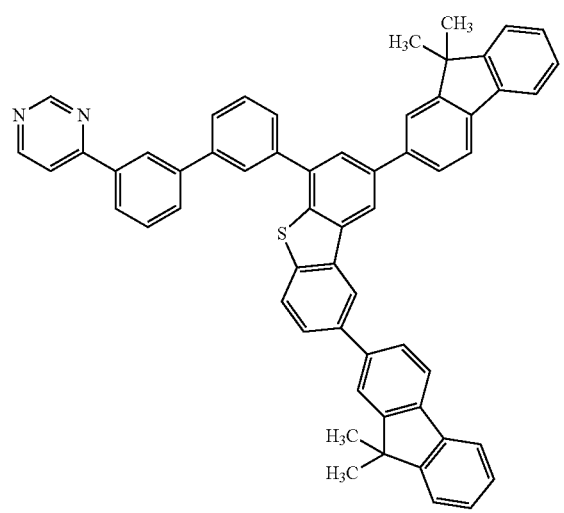
(117)
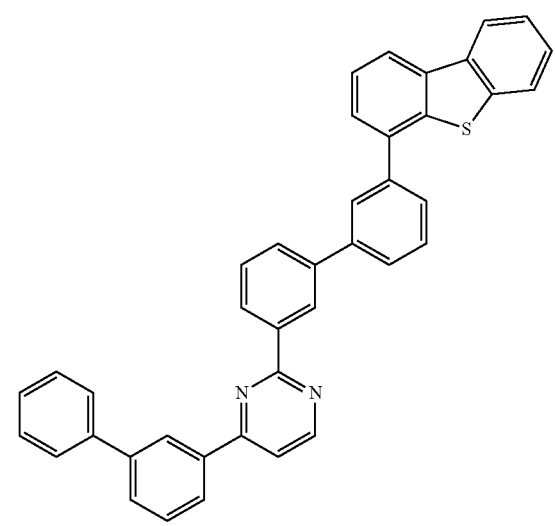
(118)
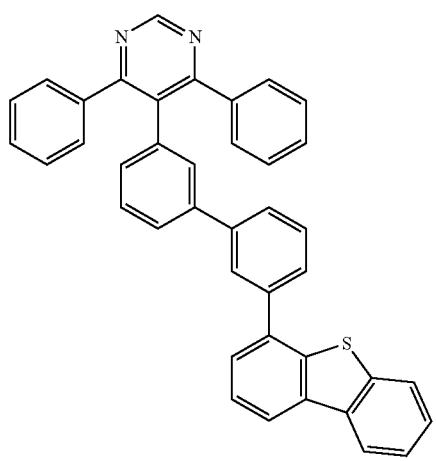

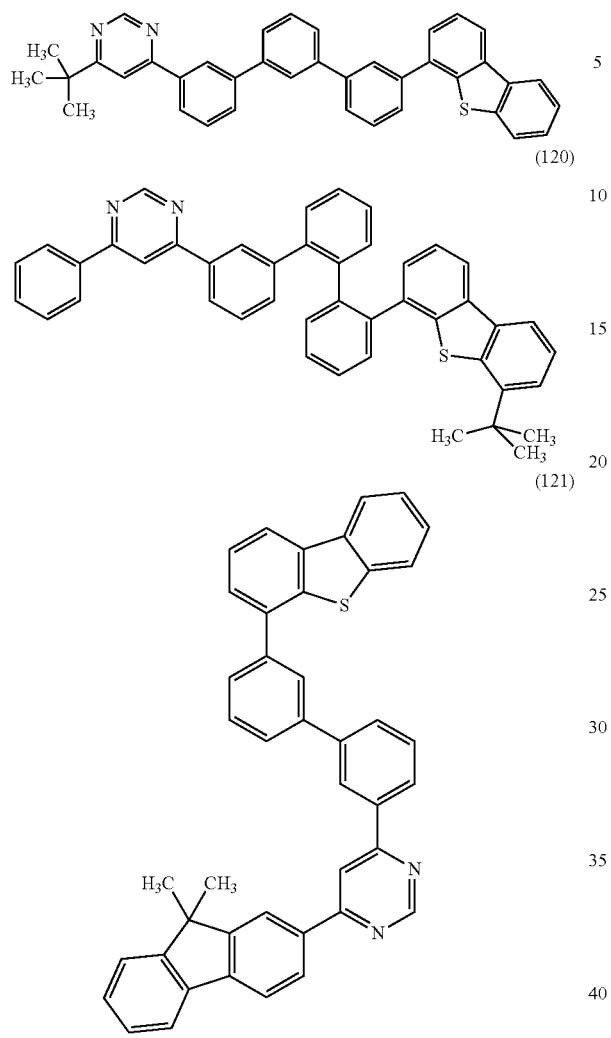

A variety of reactions can be applied as a method for synthesizing any of the heterocyclic compounds of embodiments of the present invention. For example, reactions described below enable the synthesis of the heterocyclic compound of one embodiment of the present invention represented by General Formula (G1). Note that the methods for synthesizing the heterocyclic compound of one embodiment of the present invention are not limited to the synthesis methods below.

<<Method for Synthesizing Heterocyclic Compound Represented by General Formula (G1)>>

Synthesis Scheme (A) of the heterocyclic compound represented by General Formula (G1) is shown below.

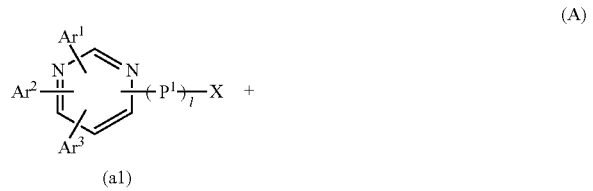

In General Formula (G1), $Ar^1$ to $Ar^a$ separately represent any of hydrogen, an alkyl group having 1 to 4 carbon atoms, a substituted or unsubstituted phenyl group, and a substituted or unsubstituted biphenyl group, and $R^1$ to $R^3$ separately represent any of hydrogen, an alkyl group having 1 to 4 carbon atoms, and a substituted or unsubstituted aryl group having 6 to 13 carbon atoms. α represents a substituted or unsubstituted phenylene group and n is 2 or 3. Z represents oxygen or sulfur.

As shown in Synthesis Scheme (A), the heterocyclic compound represented by General Formula (G1) can be obtained by making a halide of a pyrimidine derivative (a1) react with a boronic acid compound of dibenzothiophene, a derivative thereof, dibenzofuran, or a derivative thereof (a2). Note that X in the formula represents a halogen element. $P^1$ and $P^2$ each represent a substituted or unsubstituted phenylene group. l+m equals n, which is 2 or 3. $B^1$ represents a boronic acid, a boronic ester, a cyclic-triolborate salt, or the like. As the cyclic-triolborate salt, a lithium salt, a potassium salt, or a sodium salt may be used.

Note that a boronic acid compound of a pyrimidine derivative may be reacted with a halide of dibenzothiophene, a derivative thereof, dibenzofuran, or a derivative thereof.

Note that since a wide variety of the compounds (a1) and (a2) are commercially available or their synthesis is feasible, a great variety of the pyrimidine derivative represented by General Formula (G1) can be synthesized. Thus, a feature of the heterocyclic compound which is one embodiment of the present invention is the abundance of variations.

Thus, the heterocyclic compound that is one embodiment of the present invention can be synthesized.

Since the heterocyclic compounds in this embodiment that are embodiments of the present invention have high heat resistance, by fabricating a light-emitting element with the use of any of these materials, the light-emitting element can have a long lifetime. Further, since the heterocyclic compounds that are embodiments of the present invention have high electron-transport properties, any of the heterocyclic compounds can be suitably used as a material for an electron-injection layer, an electron-transport layer, or a light-emitting layer in a light-emitting element. Furthermore, when the heterocyclic compound that is one embodiment of the present invention is combined with another material to form an exciplex in a light-emitting element, the light-emitting element can have a long lifetime and high emission efficiency.
(Embodiment 2)

In this embodiment, a concept and a specific structure of a light-emitting element which utilizes an exciplex and to which any of the heterocyclic compounds of embodiments of the present invention described in Embodiment 1 is applied will be described.

Note that a light-emitting element described in this embodiment includes, between a pair of electrodes, a light-emitting layer which contains a first organic compound, a second organic compound, and a light-emitting substance converting triplet excitation energy into light. A combination of the first organic compound and the second organic compound can form an exciplex, and in the light-emitting layer, the light-emitting substance converting triplet excitation energy into light emits light owing to energy transfer from the exciplex.

Here, a process of exciplex formation in a light-emitting layer of a light-emitting element of one embodiment of the present invention will be described. There are two possible formation processes, which are described below.

In one process, an exciplex is formed from the first organic compound with an electron-transport property (e.g., a host material) and the second organic compound with a skeleton represented by General Formula (G1) which have carriers (cation or anion). Note that in such a formation process, formation of a singlet exciton from the first organic compound and the second organic compound can be suppressed, which enables the light-emitting element to have a long lifetime.

The other formation process is an elementary process where one of the first organic compound with an electron-transport property (e.g., a host material) and the second organic compound with the skeleton represented by General Formula (G1) forms a singlet exciton and then interacts with the other in a ground state to form an exciplex. In this case, although the first organic compound or the second organic compound is brought into a singlet excited state at first, the singlet excited state is rapidly converted into an exciplex; thus, deactivation of the singlet excitation energy, reaction from the singlet excited state, and the like can be suppressed also in this case, so that the light-emitting element can have a long lifetime.

Note that in a light-emitting element that is one embodiment of the present invention, an exciplex may be formed in either of the two formation processes.

FIG. 1 shows formation of levels of an exciplex which is formed through the above formation process, and a process for light emission in a light-emitting layer of a light-emitting element that is one embodiment of the present invention. As shown in FIG. 1, a difference between an $S_1$ level and a $T_1$ level of an exciplex 10 formed in the light-emitting layer of the light-emitting element is extremely small as compared to a difference between an $S_1$ level and a $T_1$ level of each of the substances (first organic compound and second organic compound) before exciplex formation. Thus, when an absorption spectrum of a light-emitting substance 11 which is contained in the light-emitting layer and converts triplet excitation energy into light largely overlaps with an emission spectrum of the exciplex formed in the light-emitting layer, not only $T_1$ energy but also $S_1$ energy generated in the exciplex can be efficiently transferred to the light-emitting substance which converts triplet excitation energy into light. As a result, emission efficiency of the light-emitting element can be considerably enhanced.

Next, a structure of a light-emitting element that is one embodiment of the present invention will be described with reference to FIG. 2.

Figure 2:
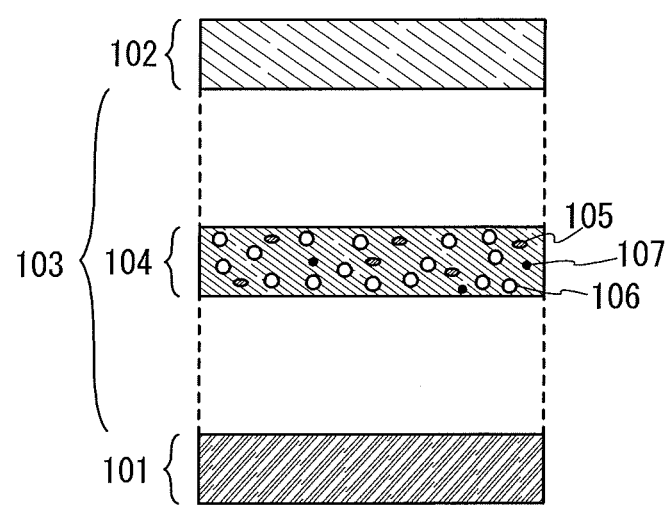
FIG. 2 illustrates a structure of a light-emitting element.

As illustrated in FIG. 2, the light-emitting element that is one embodiment of the present invention includes, between a pair of electrodes (an anode 101 and a cathode 102), a light-emitting layer 104 which contains a first organic compound 105, a second organic compound 106, and a light-emitting substance 107; the first organic compound 105 includes one pyrimidine ring and one ring with a hole-transport skeleton; the second organic compound 106 is an aromatic amine; and the light-emitting substance 107 converts triplet excitation energy into light. The light-emitting layer 104 is one of functional layers included in an EL layer 103 which is in contact with the pair of electrodes. The EL layer 103 can include, in addition to the light-emitting layer 104, any of a hole-injection layer, a hole-transport layer, an electron-transport layer, an electron-injection layer, and the like as appropriate at given positions.

The first organic compound 105, which includes the one pyrimidine ring and the one ring with the hole-transport skeleton, is a heterocyclic compound that is one embodiment of the present invention and has the structure represented by General Formula (G1).

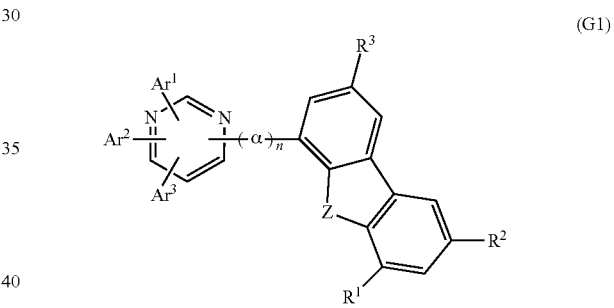

(G1)

In the formula, $Ar^1$ to $Ar^3$ separately represent any of hydrogen, an alkyl group having 1 to 4 carbon atoms, a substituted or unsubstituted phenyl group, and a substituted or unsubstituted biphenyl group, and $R^1$ to $R^3$ separately represent any of hydrogen, an alkyl group having 1 to 4 carbon atoms, and a substituted or unsubstituted aryl group having 6 to 13 carbon atoms. α represents a substituted or unsubstituted phenylene group and n is 2 or 3. Z represents oxygen or sulfur.

Note that Embodiment 1 can be referred to for specific examples of the first organic compound represented by General Formula (G1); thus, the description is not repeated here.

The following are examples of the second organic compound 106 that is an aromatic amine: a compound having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(Spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-

4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl] Spiro-9,9'-bifluoren-2-amine (abbreviation: PCBASF); and a compound having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP).

Note that the first organic compound 105 and the second organic compound 106 are not limited to the above substances as long as a combination of the first organic compound 105 and the second organic compound 106 can form an exciplex.

Further, as the light-emitting substance 107 which converts triplet excitation energy into light, a phosphorescent compound (e.g., an organometallic complex), a thermally activated delayed fluorescence (TADF) material, or the like is preferably used.

Note that examples of the organometallic complex include bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: Ir($CF_3$ppy)$_2$(pic)), bis[2-(4',6'-difluorophenyl)pyridinato-N,$C^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III) acetylacetonate (abbreviation: Ir(dpo)$_2$(acac)), bis{2-[4'-(perfluorophenyl)phenyl]pyridinato-N,$C^{2'}$}iridium(III) acetylacetonate (abbreviation: Ir(p-PF-ph)$_2$(acac)), bis(2-phenylbenzothiazolato-N,$C^{2'}$)iridium(III) acetylacetonate (abbreviation: Ir(bt)$_2$(acac)), bis[2-(2'-benzo[4,5-α]thienyl)pyridinato-N,$C^{3'}$]iridium(III) acetylacetonate (abbreviation: Ir(btp)$_2$(acac)), bis(1-phenylisoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphyrin platinum(II) (abbreviation: PtOEP), tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), and tris [1-(2-thenoyl)-3,3,3-trifluoroacetonato](monophenanthroline)europium(III) (abbreviation: Eu(TTA)$_3$(Phen)).

In the light-emitting element in this embodiment that is one embodiment of the present invention, a heterocyclic compound with high heat resistance that is one embodiment of the present invention is used for the light-emitting layer; moreover, the combination of the heterocyclic compound and the second organic compound that is an aromatic amine can form an exciplex in the light-emitting layer. Accordingly, efficiency of energy transfer from the exciplex to the light-emitting substance converting triplet excitation energy into light can be increased, so that the light-emitting element can have a long lifetime and high emission efficiency.

(Embodiment 3)

In this embodiment, an example of a light-emitting element in one embodiment of the present invention is described with reference to FIG. 3.

Figure 3:
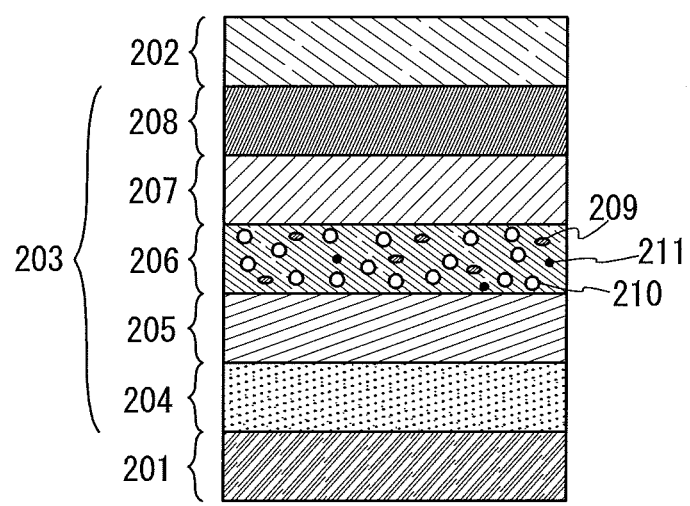
FIG. 3 illustrates a structure of a light-emitting element.

In the light-emitting element described in this embodiment, as illustrated in FIG. 3, an EL layer 203 including a light-emitting layer 206 is provided between a pair of electrodes (a first electrode (anode) 201 and a second electrode (cathode) 202), and the EL layer 203 includes a hole-injection layer 204, a hole-transport layer 205, an electron-transport layer 207, an electron-injection layer 208, and the like in addition to the light-emitting layer 206.

In a manner similar to that of the light-emitting element described in Embodiment 2, the light-emitting layer 206 includes a first organic compound 209 that is a heterocyclic compound described in Embodiment 1, a second organic compound 210 that is an aromatic amine, and a light-emitting substance 211 converting triplet excitation energy into light. Since any of the substances described in Embodiments 1 and 2 can be used for the first organic compound 209, the second organic compound 210, and the light-emitting substance 211 converting triplet excitation energy into light, the description thereof is not repeated here.

For the first electrode (anode) 201 and the second electrode (cathode) 202, a metal, an alloy, an electrically conductive compound, a mixture thereof, or the like can be used. Specifically, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), or titanium (Ti) can be used. In addition, an element belonging to Group 1 or Group 2 of the periodic table, for example, an alkali metal such as lithium (Li) or cesium (Cs), an alkaline earth metal such as magnesium (Mg), calcium (Ca), or strontium (Sr), an alloy containing such an element (e.g., MgAg or AlLi), a rare earth metal such as europium (Eu) or ytterbium (Yb), an alloy containing such an element, graphene, or the like can be used. The first electrode (anode) 201 and the second electrode (cathode) 202 can be formed by, for example, a sputtering method, an evaporation method (including a vacuum evaporation method), or the like.

Examples of a substance having a high hole-transport property which is used for the hole-injection layer 204 and the hole-transport layer 205 include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances mentioned here are mainly substances that have a hole mobility of $10^{-6}$ $cm^2$/Vs or more.

Note that other than these substances, any substance that has a hole-transport property higher than an electron-transport property may be used.

Still other examples include high molecular compounds such as poly(N-vinylcarbazole) (abbreviation: PVK), poly(4-vinyltriphenylamine) (abbreviation: PVTPA), poly [N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD).

Further, examples of an acceptor substance which can be used for the hole-injection layer 204 include oxides of transition metals, oxides of metals belonging to Groups 4 to 8 of the periodic table, and the like. Specifically, molybdenum oxide is particularly preferable.

As described above, the light-emitting layer 206 includes the first organic compound 209 with an electron-transport property and the second organic compound 210 with the skeleton represented by General Formula (G 1) (and may further include a light-emitting substance converting triplet excitation energy into light).

The electron-transport layer 207 is a layer that contains a substance having a high electron-transport property. For the electron-transport layer 207, it is possible to use a metal complex such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, or bis[2-(2-hydroxyphenyl)benzothiazolato]zinc (abbreviation: $Zn(BTZ)_2$). Alternatively, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). Further alternatively, it is possible to use a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy). The substances mentioned here are mainly substances that have an electron mobility of $10^{-6}$ $cm^2/Vs$ or more. Note that other than these substances, any substance that has an electron-transport property higher than a hole-transport property may be used for the electron-transport layer 207.

The electron-transport layer 207 is not limited to a single layer, and may be a stack of two or more layers containing any of the above substances.

The electron-injection layer 208 is a layer that contains a substance having a high electron-injection property. Examples of the substance that can be used for the electron-injection layer 208 include alkali metals, alkaline earth metals, and compounds thereof, such as lithium fluoride (LiF), cesium fluoride (CsF), calcium fluoride ($CaF_2$), and lithium oxide ($LiO_x$), and rare earth metal compounds, such as erbium fluoride ($ErF_3$). Alternatively, the above-mentioned substances for forming the electron-transport layer 207 can be used.

Alternatively, a composite material in which an organic compound and an electron donor (a donor) are mixed may be used for the electron-injection layer 208. Such a composite material, in which electrons are generated in the organic compound by the electron donor, has high electron-injection and electron-transport properties. The organic compound here is preferably a material excellent in transporting the generated electrons, and specifically any of the above substances (such as metal complexes and heteroaromatic compounds) for the electron-transport layer 207 can be used. As the electron donor, a substance showing an electron-donating property with respect to the organic compound may be used. Specifically, alkali metals, alkaline earth metals, and rare earth metals are preferable, and lithium, cesium, magnesium, calcium, erbium, ytterbium, and the like can be given. Any of alkali metal oxides and alkaline earth metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 204, the hole-transport layer 205, the light-emitting layer 206, the electron-transport layer 207, and the electron-injection layer 208 which are mentioned above can each be formed by a method such as an evaporation method (including a vacuum evaporation method), an inkjet method, or a coating method.

Light emission obtained in the light-emitting layer 206 of the above-described light-emitting element is extracted to the outside through either the first electrode 201 or the second electrode 202 or both. Thus, either the first electrode 201 or the second electrode 202 in this embodiment, or both, is an electrode having a light-transmitting property.

In the light-emitting layer of the light-emitting element in this embodiment, an exciplex is generated from the first organic compound 209, which is a heterocyclic compound of one embodiment of the present invention, and the second organic compound 210. Efficiency of energy transfer from the generated exciplex to the light-emitting substance 211 converting triplet excitation energy into light can be increased, so that the light-emitting element can have a long lifetime and high emission efficiency.

Note that the light-emitting element described in this embodiment is one embodiment of the present invention and is particularly characterized by the structure of the light-emitting layer. Thus, when the structure described in this embodiment is employed, a passive matrix light-emitting device, an active matrix light-emitting device, and the like can be manufactured. Each of these light-emitting devices is included in the present invention.

Note that there is no particular limitation on the structure of a TFT in the case of manufacturing the active matrix light-emitting device. For example, a staggered TFT or an inverted staggered TFT can be used as appropriate. Further, a driver circuit formed over a TFT substrate may be formed using both an n-type TFT and a p-type TFT or either an n-type TFT or a p-type TFT. Furthermore, there is also no particular limitation on the crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 4)

In this embodiment, as one embodiment of the present invention, a light-emitting element (hereinafter referred to as tandem light-emitting element) in which a charge generation layer is provided between a plurality of EL layers will be described.

Figure 4A:
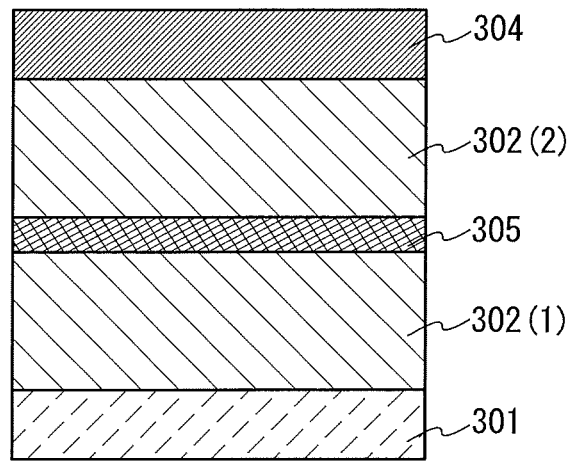
FIGS. 4A and 4B illustrate structures of light-emitting elements.

The light-emitting element described in this embodiment is a tandem light-emitting element including a plurality of EL layers (a first EL layer 302(1) and a second EL layer 302(2))

between a pair of electrodes (a first electrode 301 and a second electrode 304) as illustrated in FIG. 4A.

In this embodiment, the first electrode 301 functions as an anode, and the second electrode 304 functions as a cathode. Note that the first electrode 301 and the second electrode 304 can have structures similar to those described in Embodiment 1. In addition, all or any of the plurality of EL layers (the first EL layer 302(1) and the second EL layer 302(2)) may have structures similar to those described in Embodiment 1 or 2. In other words, the structures of the first EL layer 302(1) and the second EL layer 302(2) may be the same or different from each other and can be similar to those of the EL layers described in Embodiment 1 or 2.

Further, a charge generation layer 305 is provided between the plurality of EL layers (the first EL layer 302(1) and the second EL layer 302(2)). The charge generation layer 305 has a function of injecting electrons into one of the EL layers and injecting holes into the other of the EL layers when voltage is applied between the first electrode 301 and the second electrode 304. In this embodiment, when voltage is applied such that the potential of the first electrode 301 is higher than that of the second electrode 304, the charge generation layer 305 injects electrons into the first EL layer 302(1) and injects holes into the second EL layer 302(2).

Note that in terms of light extraction efficiency, the charge generation layer 305 preferably has a light-transmitting property with respect to visible light (specifically, the charge generation layer 305 preferably has a visible light transmittance of 40% or more). Further, the charge generation layer 305 functions even if it has lower conductivity than the first electrode 301 or the second electrode 304.

The charge generation layer 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case where the electron acceptor is added to the organic compound having a high hole-transport property, examples of the organic compound having a high hole-transport property include aromatic amine compounds such as NPB, TPD, TDATA, MTDATA, and 4,4'-bis[N-(spiro-9,9'-bifluoren-2-yl)-N-phenylamino] biphenyl (abbreviation: BSPB), and the like. The substances mentioned here are mainly substances that have a hole mobility of $10^{-6}$ cm$^2$/Vs or more. Note that other than these substances, any organic compound that has a hole-transport property higher than an electron-transport property may be used.

Examples of the electron acceptor include 7,7,8,8-tetracyano-2,3,5,6-tetrafluoroquinodimethane (abbreviation: $F_4$-TCNQ), chloranil, oxides of transition metals, and oxides of metals that belong to Groups 4 to 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting property. Among these, molybdenum oxide is especially preferable since it is stable in the air, has a low hygroscopic property, and is easy to handle.

On the other hand, in the case where the electron donor is added to the organic compound having a high electron-transport property, examples of the organic compound having a high electron-transport property which can be used are metal complexes having a quinoline skeleton or a benzoquinoline skeleton, such as Alq, Almq$_3$, BeBq$_2$, and BAlq, and the like. Other examples are metal complexes having an oxazole-based or thiazole-based ligand, such as Zn(BOX)$_2$ and Zn(BTZ)$_2$. Other than metal complexes, PBD, OXD-7, TAZ, BPhen, BCP, or the like can be used. The substances mentioned here are mainly substances that have an electron mobility of $10^{-6}$ cm$^2$/Vs or more. Note that other than these substances, any organic compound that has an electron-transport property higher than a hole-transport property may be used.

Examples of the electron donor which can be used are alkali metals, alkaline earth metals, rare earth metals, metals that belong to Group 13 of the periodic table, and oxides or carbonates thereof. Specifically, lithium (Li), cesium (Cs), magnesium (Mg), calcium (Ca), ytterbium (Yb), indium (In), lithium oxide, cesium carbonate, and the like are preferable. An organic compound, such as tetrathianaphthacene, may be used as the electron donor.

Note that forming the charge generation layer 305 by using any of the above materials can suppress a drive voltage increase caused by the stack of the EL layers.

Figure 4B:
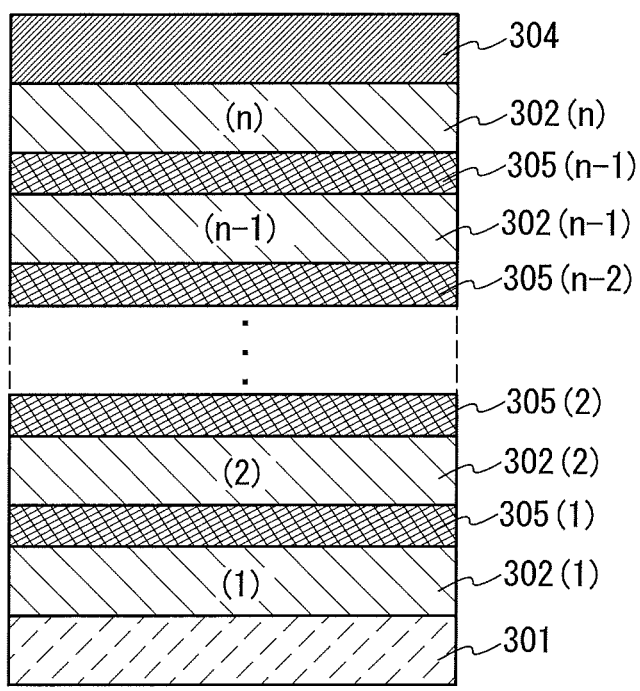

Although this embodiment shows the light-emitting element having two EL layers, the present invention can be similarly applied to a light-emitting element in which n EL layers (n is 3 or more) are stacked as illustrated in FIG. 4B. In the case where a plurality of EL layers are included between a pair of electrodes as in the light-emitting element in this embodiment, by provision of the charge generation layers between the EL layers, light emission in a high luminance region can be obtained with current density kept low. Since the current density can be kept low, the element can have a long lifetime. When the light-emitting element is applied to lighting, voltage drop due to resistance of an electrode material can be reduced, thereby achieving homogeneous light emission in a large area. Moreover, it is possible to achieve a light-emitting device which can be driven at low voltage and has low power consumption.

Furthermore, by making emission colors of EL layers different, light of a desired color can be obtained from the light-emitting element as a whole. For example, the emission colors of first and second EL layers are complementary in a light-emitting element having the two EL layers, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors.

Further, the same applies to a light-emitting element having three EL layers. For example, the light-emitting element as a whole can emit white light when the emission color of the first EL layer is red, the emission color of the second EL layer is green, and the emission color of the third EL layer is blue.

As well as the structure in this embodiment in which the EL layers are stacked with the charge generation layer provided therebetween, the light-emitting element may have a micro optical resonator (microcavity) structure which utilizes a light resonant effect by adjusting a distance between the electrodes (the first electrode 301 and the second electrode 304) to a desired value.

Note that the structure described in this embodiment can be combined as appropriate with any of the structures described in the other embodiments.

(Embodiment 5)

In this embodiment, a light-emitting device including a light-emitting element which is one embodiment of the present invention will be described.

Note that any of the light-emitting elements described in the other embodiments can be used as the light-emitting element. Further, although either of a passive matrix light-emitting device and an active matrix light-emitting device may be used as the light-emitting device, an active matrix light-emitting device will be described in this embodiment with reference to FIGS. 5A and 5B.

Figure 5A:
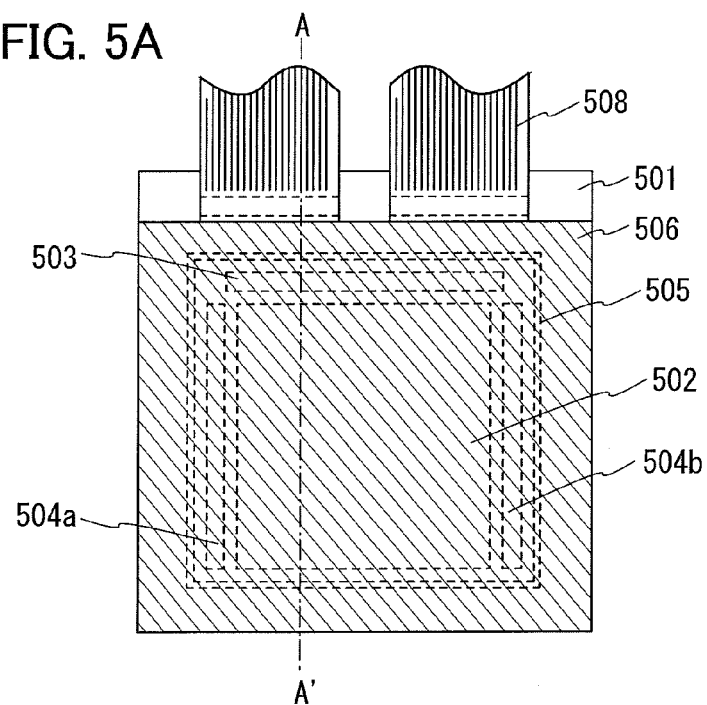
FIGS. 5A and 5B illustrate a light-emitting device.
Figure 5B:
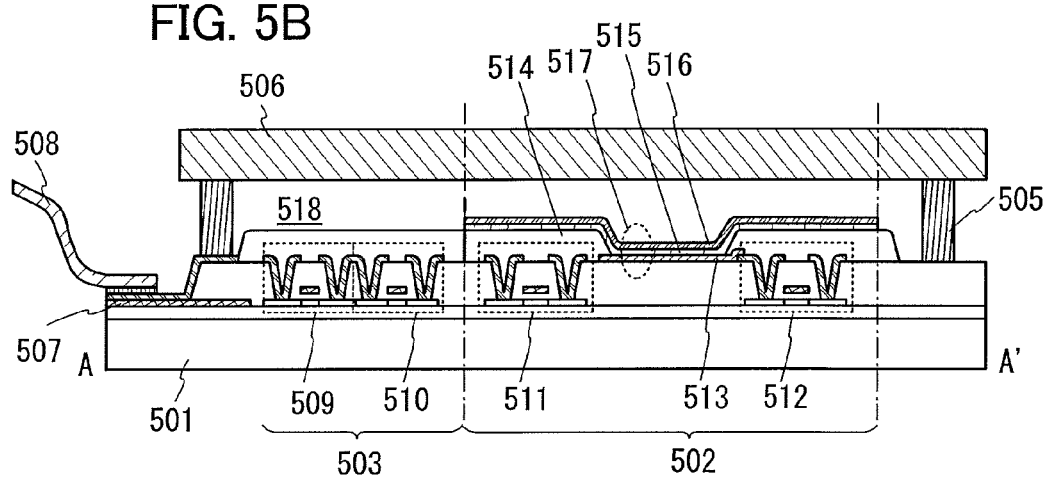

Note that FIG. 5A is a top view illustrating a light-emitting device and FIG. 5B is a cross-sectional view taken along the chain line A-A' in FIG. 5A. The active matrix light-emitting device in this embodiment includes a pixel portion 502 provided over an element substrate 501, a driver circuit portion (a source line driver circuit) 503, and driver circuit portions (gate line driver circuits) 504a and 504b. The pixel portion 502, the driver circuit portion 503, and the driver circuit portions 504a and 504b are sealed between the element substrate 501 and a sealing substrate 506 with a sealant 505.

In addition, there is provided a lead wiring 507 over the element substrate 501. The lead wiring 507 is provided for connecting an external input terminal through which a signal (e.g., a video signal, a clock signal, a start signal, or a reset signal) or a potential from the outside is transmitted to the driver circuit portion 503 and the driver circuit portions 504a and 504b. Here is shown an example in which a flexible printed circuit (FPC) 508 is provided as the external input terminal. Although only the FPC is illustrated, this FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 5B. The driver circuit portions and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using any of various circuits, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 502 includes a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a curvature radius (0.2 µm to 3 µm) at the upper end portion. The insulator 514 can be formed using either a negative photosensitive resin or a positive photosensitive resin. The material of the insulator 514 is not limited to an organic compound and an inorganic compound such as silicon oxide or silicon oxynitride can also be used.

An EL layer 515 and a second electrode (cathode) 516 are stacked over the first electrode (anode) 513, so that a light-emitting element 517 is formed. Note that the EL layer 515 includes at least the light-emitting layer described in Embodiment 1. Further, in the EL layer 515, a hole-injection layer, a hole-transport layer, an electron-transport layer, an electron-injection layer, a charge generation layer, and the like can be provided as appropriate in addition to the light-emitting layer.

For the first electrode (anode) 513, the EL layer 515, and the second electrode (cathode) 516, the materials described in Embodiment 2 can be used. Although not illustrated, the second electrode (cathode) 516 is electrically connected to the FPC 508 which is an external input terminal.

Although the cross-sectional view in FIG. 5B illustrates only one light-emitting element 517, a plurality of light-emitting elements are arranged in a matrix in the pixel portion 502. Light-emitting elements which provide three kinds of light emission (R, and B) are selectively formed in the pixel portion 502, whereby a light-emitting device capable of full color display can be fabricated. Alternatively, a light-emitting device capable of full color display may be fabricated by a combination with color filters.

Further, the sealing substrate 506 is attached to the element substrate 501 with the sealant 505, whereby the light-emitting element 517 is provided in a space 518 surrounded by the element substrate 501, the sealing substrate 506, and the sealant 505. The space 518 may be filled with an inert gas (such as nitrogen or argon) or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), poly (vinyl fluoride) (PVF), polyester, acrylic, or the like can be used.

As described above, an active matrix light-emitting device can be obtained.

Note that the structure described in this embodiment can be combined as appropriate with any of the structures described in the other embodiments.

(Embodiment 6)

In this embodiment, examples of a variety of electronic devices which are completed using a light-emitting device will be described with reference to FIGS. 6A to 6D and FIGS. 7A to 7C. The light-emitting device is fabricated using a light-emitting element which is one embodiment of the present invention.

Examples of electronic devices to which the light-emitting device is applied are television devices (also referred to as TV or television receivers), monitors for computers and the like, cameras such as digital cameras and digital video cameras, digital photo frames, cellular phones (also referred to as mobile phones or mobile phone devices), portable game machines, portable information terminals, audio playback devices, large game machines such as pin-ball machines, and the like. Specific examples of these electronic devices are illustrated in FIGS. 6A to 6D.

Figure 6A:
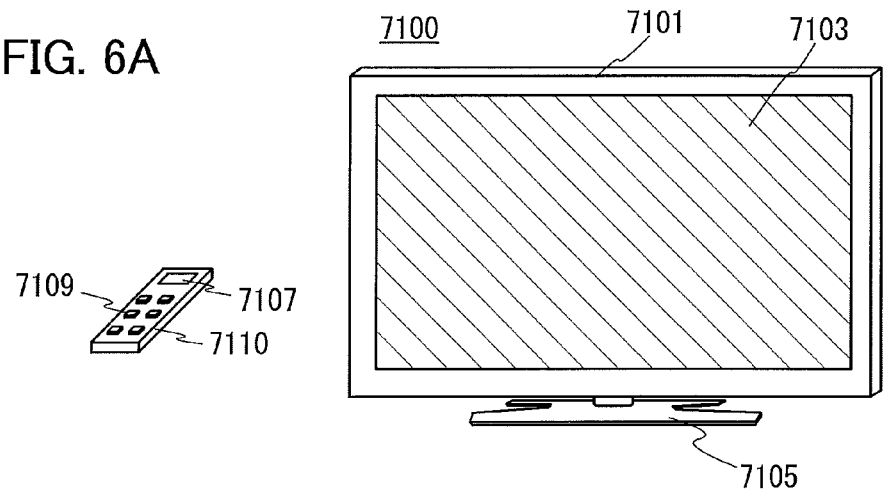
FIGS. 6A to 6D illustrate electronic devices.

FIG. 6A illustrates an example of a television device. In a television device 7100, a display portion 7103 is incorporated in a housing 7101. The display portion 7103 is capable of displaying images, and the light-emitting device can be used for the display portion 7103. In addition, here, the housing 7101 is supported by a stand 7105.

The television device 7100 can be operated with an operation switch provided in the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 6B:
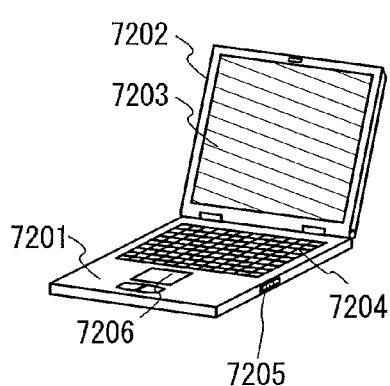

FIG. 6B illustrates a computer, which includes a main body 7201, a housing 7202, a display portion 7203, a keyboard 7204, an external connection port 7205, a pointing device 7206, and the like. Note that this computer is manufactured by using the light-emitting device for the display portion 7203.

Figure 6C:
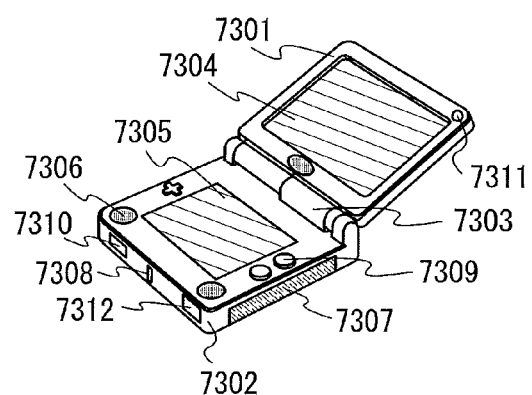

FIG. 6C illustrates a portable game machine, which includes two housings, i.e., a housing 7301 and a housing 7302, connected to each other via a joint portion 7303 so that the portable game machine can be opened or closed. A display portion 7304 is incorporated in the housing 7301 and a display portion 7305 is incorporated in the housing 7302. In addition, the portable game machine illustrated in FIG. 6C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), and a microphone 7312), and the like. It is needless to say that the structure of the portable game machine is not limited to the above structure as long as the light-emitting device is used for at least either the display portion 7304 or the display portion 7305, or both, and may include other accessories as appropriate. The portable game machine illustrated in FIG. 6C has a function of reading out a program or data stored in a storage medium to display it on the display portion, and a function of sharing information with another portable game machine by wireless communication. Note that a function of the portable game machine illustrated in FIG. 6C is not limited to the above, and the portable game machine can have a variety of functions.

Figure 6D:
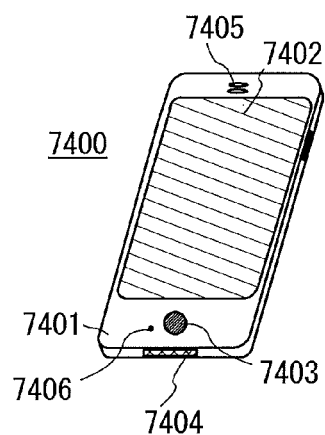

FIG. 6D illustrates an example of a cellular phone. A cellular phone 7400 is provided with a display portion 7402 incorporated in a housing 7401, operation buttons 7403, an external connection port 7404, a speaker 7405, a microphone 7406, and the like. Note that the cellular phone 7400 is manufactured using the light-emitting device for the display portion 7402.

When the display portion 7402 of the cellular phone 7400 illustrated in FIG. 6D is touched with a finger or the like, data can be input to the cellular phone 7400. Further, operations such as making a call and creating e-mail can be performed by touch on the display portion 7402 with a finger or the like.

There are mainly three screen modes for the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, the input mode mainly for inputting characters is selected for the display portion 7402 so that characters displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation buttons 7403 of the housing 7401. Alternatively, the screen modes can be changed depending on the kind of image displayed on the display portion 7402. For example, when a signal for an image to be displayed on the display portion is data of moving images, the screen mode is changed to the display mode. When the signal is text data, the screen mode is changed to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal identification can be performed. Furthermore, when a backlight or a sensing light source which emits near-infrared light is provided for the display portion, an image of a finger vein, a palm vein, or the like can also be taken.

Figure 7A:
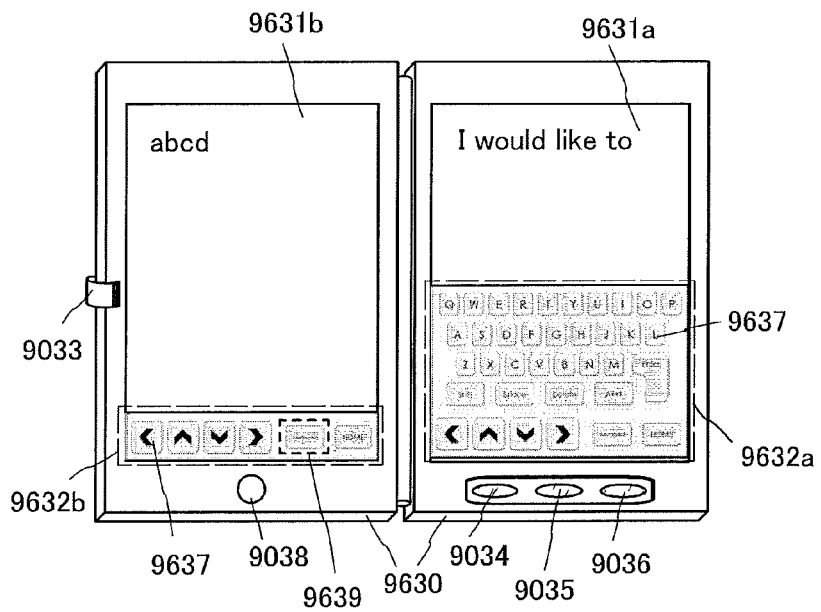
FIGS. 7A to 7C illustrate an electronic device.
Figure 7B:
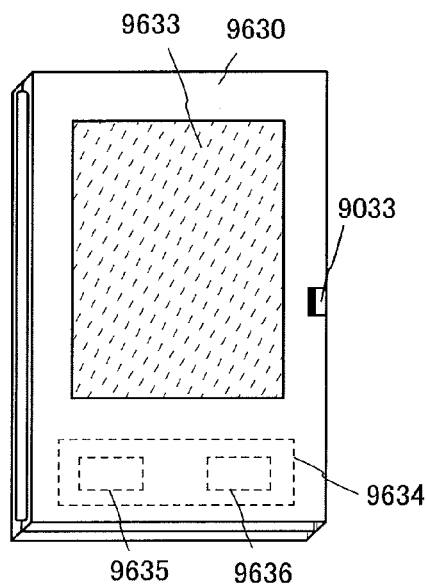

FIGS. 7A and 7B illustrate a foldable tablet terminal. The tablet terminal is opened in FIG. 7A. The tablet terminal includes a housing 9630, a display portion 9631a, a display portion 9631b, a display mode switch 9034, a power switch 9035, a power saver switch 9036, a clasp 9033, and an operation switch 9038. The tablet terminal is manufactured using the light-emitting device for either the display portion 9631a or the display portion 9631b or both.

Part of the display portion 9631a can be a touch panel region 9632a and data can be input when a displayed operation key 9637 is touched. Although a structure in which half of the display portion 9631a has only a display function and the other half has a touch panel function is shown as an example, one embodiment of the present invention is not limited to the structure. The whole region in the display portion 9631a may have a touch panel function. For example, the display portion 9631a can display keyboard buttons in the whole region to be a touch panel, and the display portion 9631b can be used as a display screen.

In the display portion 9631b, as in the display portion 9631a, part of the display portion 9631b can be a touch panel region 9632b. When a keyboard display switching button 9639 displayed on the touch panel is touched with a finger, a stylus, or the like, keyboard buttons can be displayed on the display portion 9631b.

Touch input can be performed in the touch panel region 9632a and the touch panel region 9632b at the same time.

The display mode switch 9034 can switch the display between a portrait mode, a landscape mode, and the like, and between monochrome display and color display, for example. The power saver switch 9036 can control display luminance in accordance with the amount of external light in use of the tablet terminal detected by an optical sensor incorporated in the tablet terminal. In addition to the optical sensor, another detection device including a sensor for detecting inclination, such as a gyroscope or an acceleration sensor, may be incorporated in the tablet terminal.

Although the display portion 9631a and the display portion 9631b have the same display area in FIG. 7A, one embodiment of the present invention is not limited to this example. One of the display portions may be different from the other display portion in size and display quality. For example, one of them may be a display panel that can display higher-definition images than the other.

The tablet terminal is closed in FIG. 7B. The tablet terminal includes the housing 9630, a solar cell 9633, a charge and discharge control circuit 9634, a battery 9635, and a DCDC converter 9636. In FIG. 7B, a structure including the battery 9635 and the DCDC converter 9636 is illustrated as an example of the charge and discharge control circuit 9634.

Since the tablet terminal is foldable, the housing 9630 can be closed when the tablet terminal is not used. As a result, the display portion 9631*a* and the display portion 9631*b* can be protected; thus, a tablet terminal which has excellent durability and excellent reliability in terms of long-term use can be provided.

In addition, the tablet terminal illustrated in FIGS. 7A and 7B can have a function of displaying a variety of kinds of data (e.g., a still image, a moving image, and a text image), a function of displaying a calendar, a date, the time, or the like on the display portion, a touch-input function of operating or editing the data displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar cell 9633 can be provided on one or both surfaces of the housing 9630 and the battery 9635 can be charged efficiently. The use of a lithium ion battery as the battery 9635 is advantageous in downsizing or the like.

The structure and the operation of the charge and discharge control circuit 9634 illustrated in FIG. 7B will be described with reference to a block diagram in FIG. 7C. The solar cell 9633, the battery 9635, the DCDC converter 9636, a converter 9638, switches SW1 to SW3, and a display portion 9631 are illustrated in FIG. 7C, and the battery 9635, the DCDC converter 9636, the converter 9638, and the switches SW1 to SW3 correspond to the charge and discharge control circuit 9634 illustrated in FIG. 7B.

First, an example of the operation in the case where power is generated by the solar cell 9633 using external light is described. The voltage of power generated by the solar cell 9633 is stepped up or down by the DCDC converter 9636 so that the power has voltage for charging the battery 9635. Then, when the power from the solar cell 9633 is used for the operation of the display portion 9631, the switch SW1 is turned on and the voltage of the power is stepped up or down by the converter 9638 so as to be voltage needed for the display portion 9631. In addition, when display on the display portion 9631 is not performed, the switch SW1 is turned off and the switch SW2 is turned on so that the battery 9635 may be charged.

Note that the solar cell 9633 is shown as an example of a power generation means; however, there is no particular limitation on a way of charging the battery 9635, and the battery 9635 may be charged using another power generation means such as a piezoelectric element or a thermoelectric conversion element (Peltier element). For example, a non-contact electric power transmission module which transmits and receives power wirelessly (without contact) to charge the battery 9635, or a combination of the solar cell 9633 and another means for charge may be used.

Figure 7C:
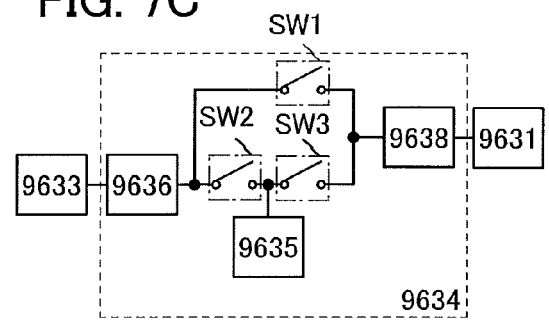

It is needless to say that one embodiment of the present invention is not limited to the electronic device illustrated in FIGS. 7A to 7C as long as the display portion described in the above embodiment is included.

As described above, the electronic devices can be obtained by the use of the light-emitting device which is one embodiment of the present invention. The light-emitting device has a remarkably wide application range, and can be applied to electronic devices in a variety of fields.

Note that the structure described in this embodiment can be combined as appropriate with any of the structures described in the other embodiments.

(Embodiment 7)

In this embodiment, examples of lighting devices will be described with reference to FIG. 8. A light-emitting device including a light-emitting element which is one embodiment of the present invention is applied to the lighting devices.

Figure 8:
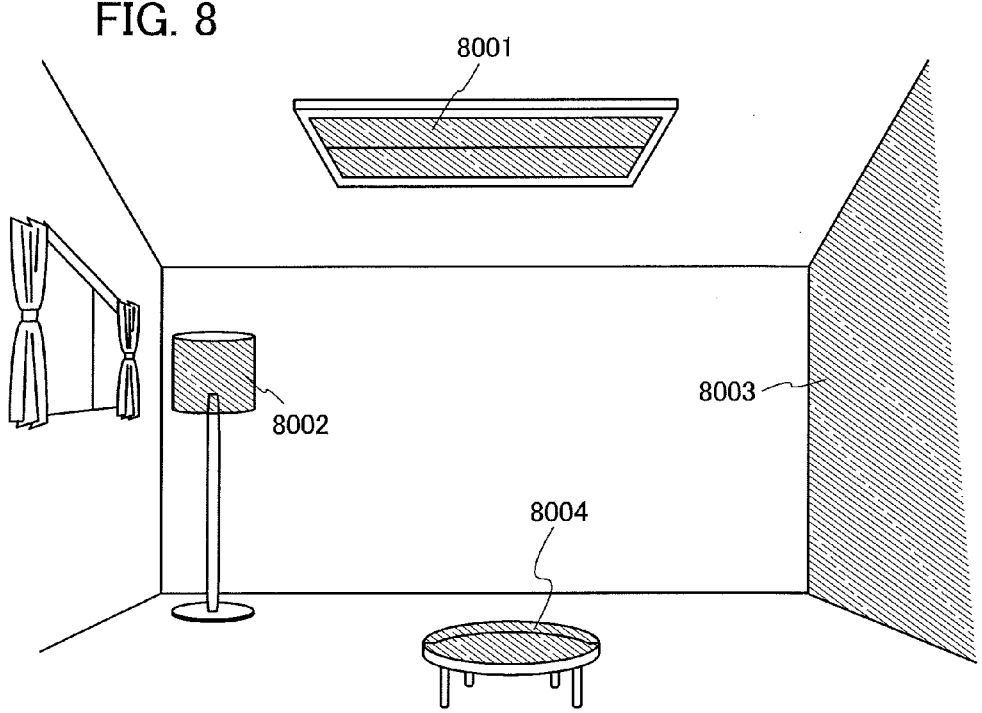
FIG. 8 illustrates lighting devices.

FIG. 8 illustrates an example in which the light-emitting device is used for an interior lighting device 8001. Since the light-emitting device can have a larger area, a lighting device having a large area can also be formed. In addition, a lighting device 8002 in which a light-emitting region has a curved surface can also be formed with the use of a housing with a curved surface. A light-emitting element included in the light-emitting device described in this embodiment is in the form of a thin film, which allows the housing to be designed more freely. Thus, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

The structure described in this embodiment can be combined as appropriate with any of the structures described in the other embodiments.

EXAMPLE 1

Synthesis Example 1

In this example, a method for synthesizing 4-[3'-(4-dibenzothienyl)-1,1'-biphenyl-3-yl]-2,6-diphenylpyrimidine (abbreviation: 2,6Ph-4mDBTBPPm-II), which is the heterocyclic compound of one embodiment of the present invention represented by Structural Formula (100) in Embodiment 1, will be described. A structure of 2,6Ph-4mDBTBPPm-II (abbreviation) is shown below.

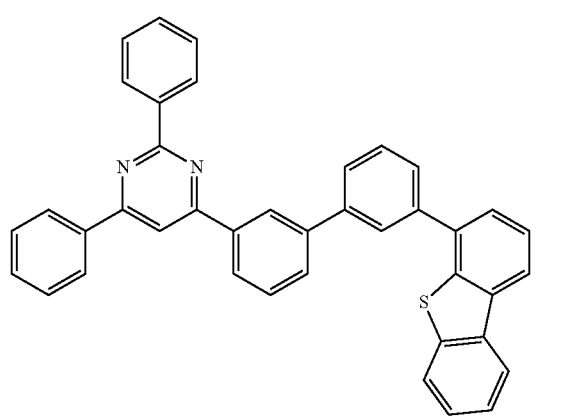

(100)

Step 1: Synthesis of 4-(3-Bromophenyl)-2,6-diphenylpyrimidine

Synthesis Scheme (B-1) of 4-(3-bromophenyl)-2,6-diphenylpyrimidine is shown below.

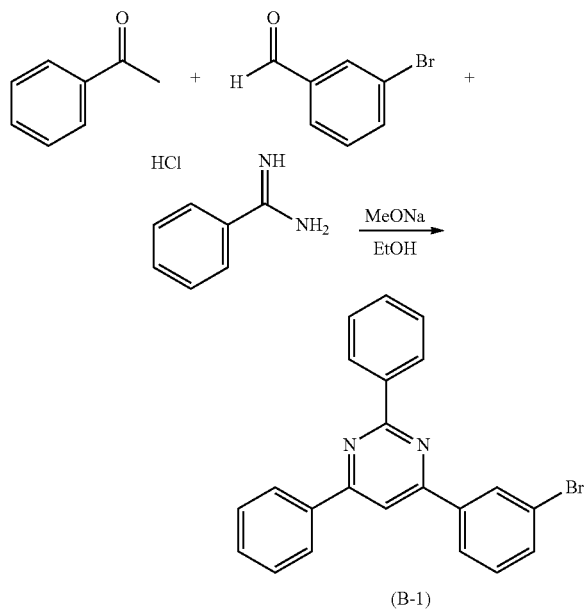

(B-1)

Into a 500-mL three-neck flask were put 18.5 g (100.0 mmol) of 3-bromobenzaldehyde and 12.0 g (100.0 mmol) of acetophenone, the air in the flask was replaced with nitrogen, and 100 mL of ethanol was added. To this mixture, 6.0 g (111.0 mmol) of sodium methoxide suspended in 100 mL of ethanol was added dropwise, and the mixture was stirred at room temperature for 22 hours. After the stirring for the predetermined time, 15.6 g (100.0 mmol) of benzamidine hydrochloride and 8.0 g (200.0 mmol) of sodium hydroxide were added and the mixture was stirred at 70° C. for 3 hours. After the stirring, the mixture was filtered. Water was added to the residue and ultrasonic cleaning was performed. A solid was collected by suction filtration, so that 14.4 g of a white solid was obtained in a yield of 38.0%.

Step 2: Synthesis of 2,6Ph-4mDBTBPPm-II (abbreviation)

Synthesis Scheme (B-2) of 2,6Ph-4mDBTBPPm-II (abbreviation) is shown below.

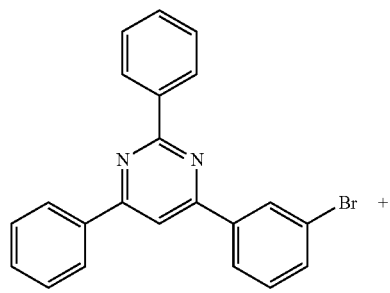

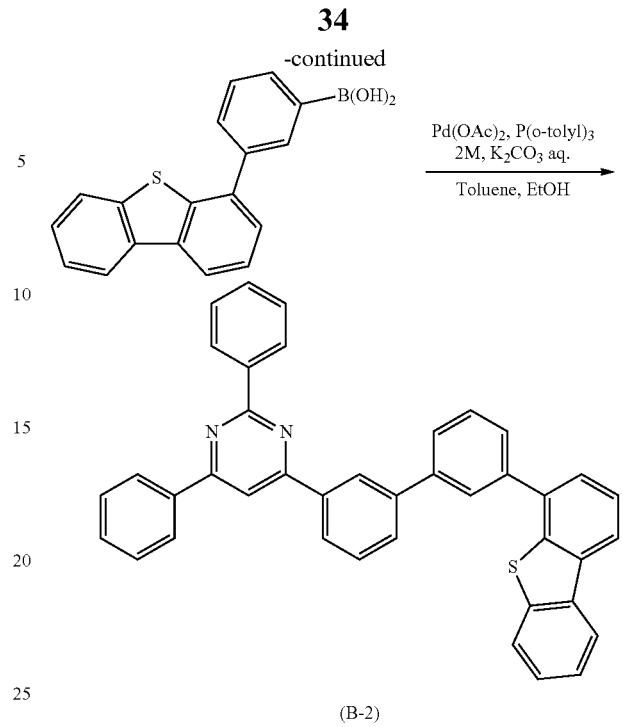

(B-2)

Into a 500-mL three-neck flask were put 7.75 g (20.0 mmol) of 4-(3-bromophenyl)-2,6-diphenylpyrimidine, 7.60 g (25.0 mmol) of 3-(dibenzothiophen-4-yl)phenylboronic acid, and 608.7 mg (2.0 mmol) of tris(o-tolyl)phosphine. To this mixture, 155 mL of toluene, 20 mL of ethanol, and 25 mL of a 2M aqueous solution of potassium carbonate were added. After this mixture was degassed while being stirred under a reduced pressure, 224.5 mg (1.0 mmol) of palladium(II) acetate was added. The mixture was heated and stirred at 80° C. under a nitrogen stream for 2.5 hours to cause a reaction. After the reaction, 1300 mL of toluene was added and an organic layer and an aqueous layer were separated. The aqueous layer was subjected to extraction with toluene. The solution of the extract and the organic layer were combined, washed with a saturated aqueous solution of sodium chloride, and dried over magnesium sulfate. After the drying, the mixture was subjected to gravity filtration. Then, filtration through Celite and alumina was performed, and the filtrate was concentrated. Recrystallization with toluene was performed to give 9.64 g of a white solid in a yield of 85.1%.

Figure 9A:
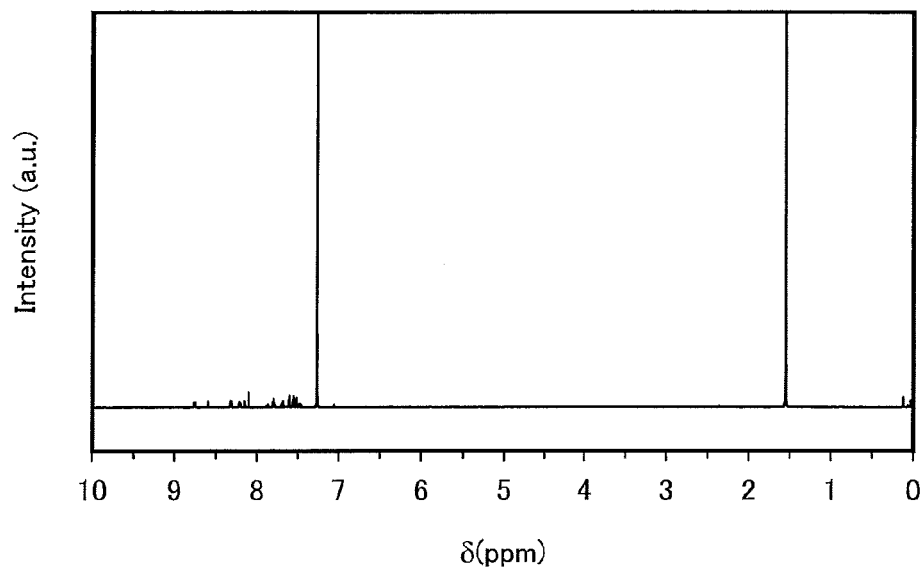
FIGS. 9A and 9B show $^1$H-NMR charts of a heterocyclic compound represented by Structural Formula (100).
Figure 9B:
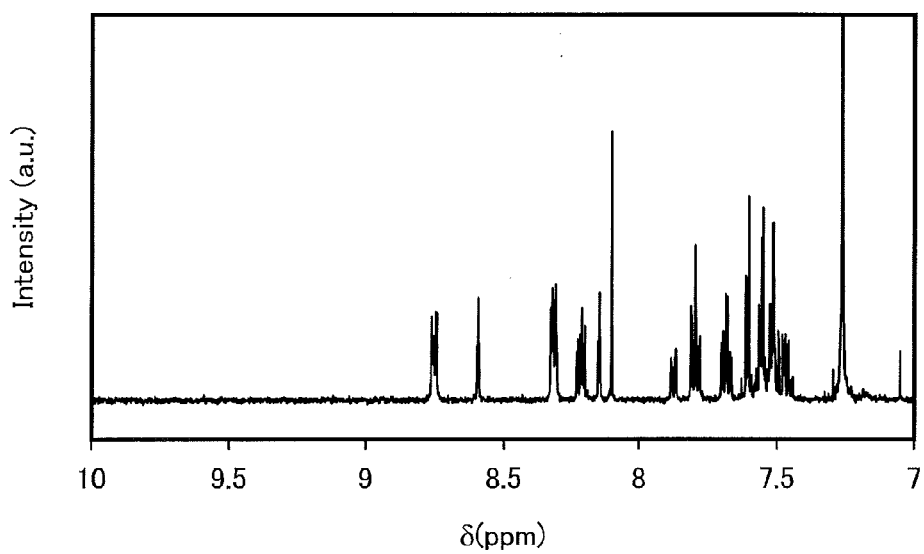

Results of analysis by nuclear magnetic resonance ($^1$H-NMR) spectroscopy of the compound obtained by the above-described synthesis method are described below. The $^1$H-NMR charts are shown in FIGS. 9A and 9B. The results reveal that 2,6Ph-4mDBTBPPm-II (abbreviation), which is the heterocyclic compound of one embodiment of the present invention represented by Structural Formula (100), was obtained.

$^1$H NMR (CDCl$_3$, 500 MHz): δ=7.46-7.61 (m, 10H), 7.66-7.70 (dt, J=2.5 Hz, 7.8 Hz, 2H), 7.78-7.81 (t, J=7.7 Hz, 3H), 7.87-7.88 (d, J=8.0 Hz, 1H), 8.01 (s, 1H), 8.14-8.15 (t, J=1.7 Hz, 1H), 8.20-8.23 (m, 2H), 8.31-8.33 (dd, J=2.3 Hz, 7.4 Hz, 3H), 8.60-8.61 (t, J=1.7 Hz, 1H), 8.74-8.63 (m, 2H).

Next, 2,6Ph-4mDBTBPPm-II (abbreviation) obtained in this example was analyzed by liquid chromatography mass spectrometry (LC/MS).

The analysis by LC/MS was carried out with Acquity UPLC (produced by Waters Corporation) and Xevo G2 T of MS (produced by Waters Corporation).

In the MS analysis, ionization was carried out by an electrospray ionization (ESI) method. Capillary voltage and sample cone voltage were set to 3.0 kV and 30 V, respectively. Detection was performed in a positive mode. A component which underwent the ionization under the above-mentioned conditions was collided with an argon gas in a collision cell to dissociate into product ions. Energy (collision energy) for the collision with argon was 70 eV. A mass range for the measurement was m/z=100-1200.

Figure 10:
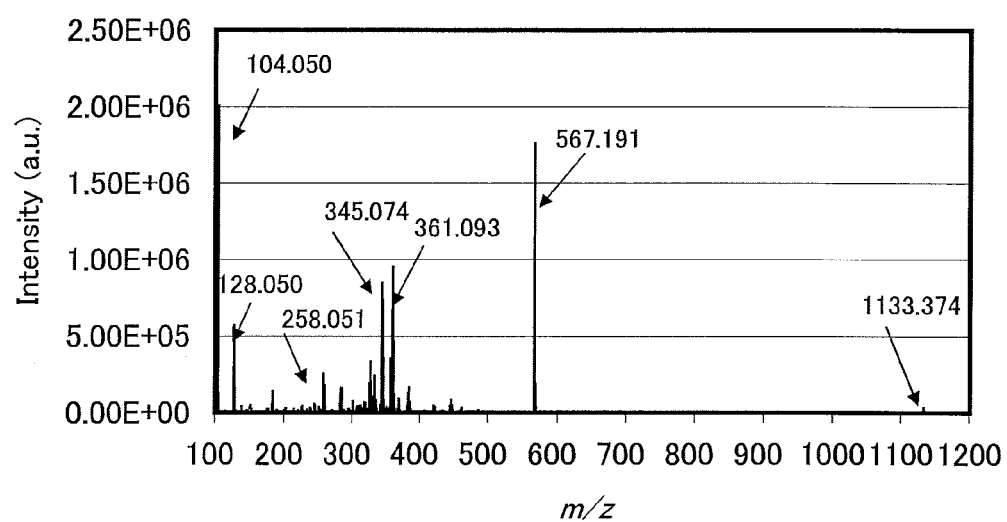
FIG. 10 shows results of LC-MS measurement of a heterocyclic compound represented by Structural Formula (100).

FIG. 10 shows the measurement results. The results in FIG. 10 show that as for 2,6Ph-4mDBTBPPm-II (abbreviation), which is the heterocyclic compound of one embodiment of the present invention represented by Structural Formula (100), product ions are detected mainly around m/z=361, m/z=345, m/z=258, m/z=128, and m/z=104. Note that the results in FIG. 10 show characteristics derived from 2,6Ph-4mDBTBPPm-II (abbreviation) and therefore can be regarded as important data for identifying 2,6Ph-4mDBTB-PPm-II (abbreviation) contained in a mixture.

It is probable that a C—C bond next to the nitrogen atom of the pyrimidine ring is cut, electric charge remains in a fragment containing the nitrogen atom, and the data appearing around m/z=361, m/z=128, and m/z=104 is thus data on a state where the C—C bond next to the nitrogen atom of the pyrimidine ring of the compound represented by Structural Formula (100) is cut; accordingly, the data is useful. In addition, the product ion around m/z=345 can be presumed to be a product ion including one dibenzothiophene ring and two benzene rings, and the product ion around m/z=258 can be presumed to be a product ion including one dibenzothiophene ring and one benzene ring; thus, it is suggested that 2,6Ph-4mDBTBPPm-II (abbreviation), which is the heterocyclic compound of one embodiment of the present invention, includes a dibenzothiophene ring.

EXAMPLE 2

Synthesis Example 2

In this example, a method for synthesizing 4-[3'-(4-dibenzothienyl)-1,1'-biphenyl-4-yl]-2,6-diphenylpyrimidine (abbreviation: 2,6Ph-4pmDBTBPPm-II), which is the heterocyclic compound of one embodiment of the present invention represented by Structural Formula (101) in Embodiment 1, will be described. A structure of 2,6Ph-4pmDBTBPPm-II (abbreviation) is shown below.

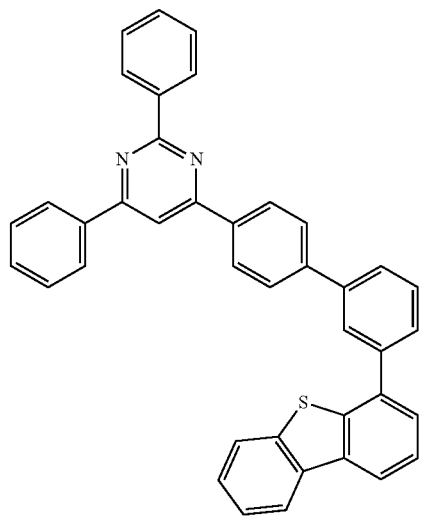

(101)

Step 1: Synthesis of 4-(4-Bromophenyl)-2,6-diphenylpyrimidine

Synthesis Scheme (C-1) of 4-(4-bromophenyl)-2,6-diphenylpyrimidine is shown below.

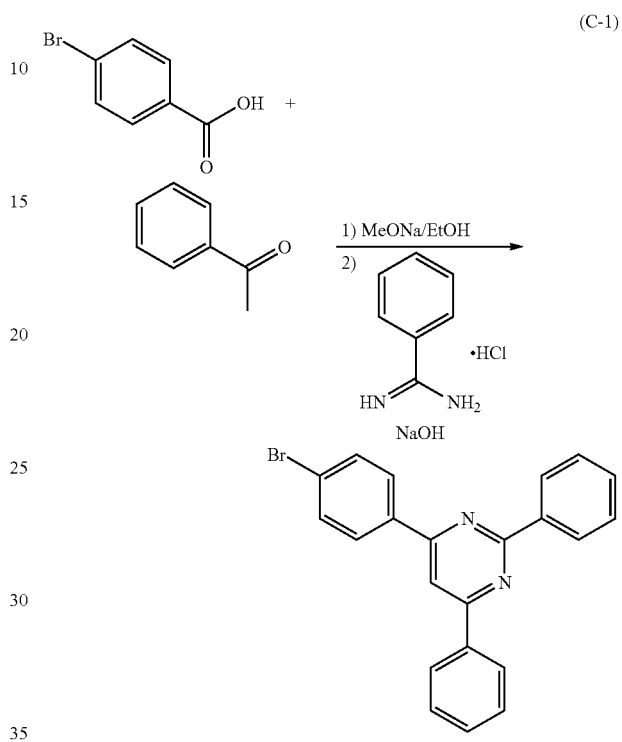

(C-1)

Into a 300-mL three-neck flask were put 11 mL (94.6 mmol) of acetophenone and 17.9 g (96.7 mmol) of 4-bromobenzaldehyde, and the air in the flask was replaced with nitrogen. To this mixture, 50 mL of ethanol was added and 5.99 g (110.9 mmol) of sodium methoxide suspended in 50 mL of ethanol was added dropwise. The mixture was stirred at room temperature for 5 hours and further stirred at 70° C. for 50 minutes. After the predetermined time elapsed, 15.1 g (96.6 mmol) of benzamidine hydrochloride and 8.03 g (200 mmol) of sodium hydroxide were added and the mixture was stirred at 70° C. for 9 hours. After the predetermined time elapsed, this mixture was suction-filtered, and the obtained residue was dissolved in chloroform and subjected to extraction with water. The obtained organic layer was washed with a saturated aqueous solution of sodium chloride and dried over magnesium sulfate. This mixture was subjected to gravity filtration, and the solvent was distilled off to give a solid. The obtained solid was washed with ethanol, so that 8.61 g of an objective white solid was obtained in a yield of 22%.

In addition, the filtrate obtained after the suction filtration was concentrated, followed by purification using silica gel column chromatography. Toluene was used as a developing solvent. The obtained fraction was concentrated and recrystallization with ethanol was performed. The obtained solid was subjected to ultrasonic cleaning using ethanol, so that 1.03 g of the objective white solid was obtained in a yield of 2.7%.

Step 2: Synthesis of 2,6Ph-4pmDBTBPPm-II (abbreviation)

Synthesis Scheme (C-2) of 2,6Ph-4pmDBTBPPm-II (abbreviation) is shown below.

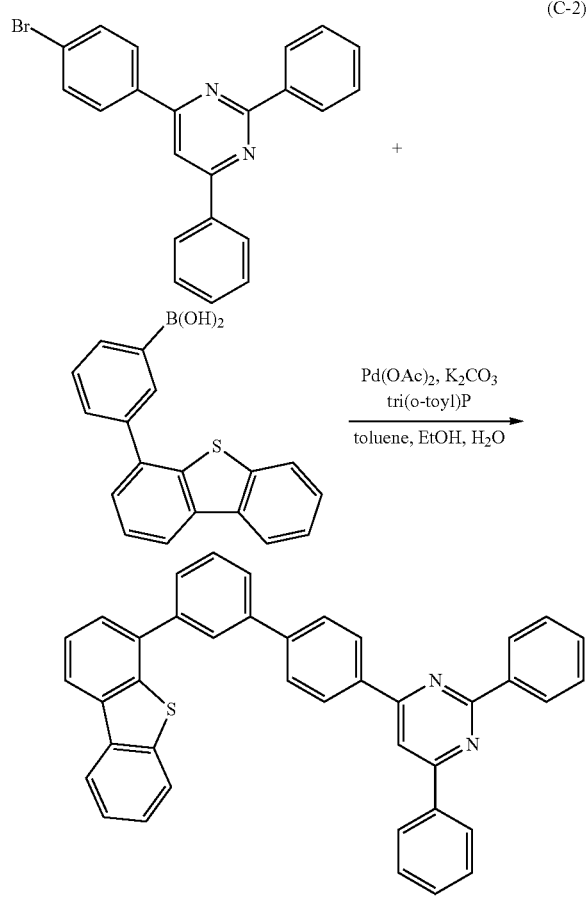

(C-2)

Into a 200-mL three-neck flask were put 5.03 g (13.0 mmol) of 4-(4-bromophenyl)-2,6-diphenylpyrimidine, 5.10 g (16.8 mmol) of 3-(dibenzothiophen-4-yl)phenylboronic acid, 0.15 g (0.49 mmol) of tris(2-methylphenyl)phosphine, 50 mL of toluene, 16 mL of ethanol, and 16 mL of a 2M aqueous solution of potassium carbonate. This mixture was degassed by being stirred while the pressure was reduced, and after the degasification, 64 mg (0.29 mmol) of palladium acetate was added. The mixture was stirred at 90° C. under a nitrogen stream for 3 hours. After the predetermined time elapsed, this mixture was subjected to suction filtration. Water was added to the obtained filtrate, and the aqueous layer was subjected to extraction with toluene. The solution of the extract combined with the organic layer was washed with water and a saturated aqueous solution of sodium chloride and dried over magnesium sulfate. The mixture was subjected to gravity filtration. The obtained filtrate was concentrated and combined with the residue collected after the suction filtration, and was dissolved in hot toluene. The mixture was suction-filtered through Celite, alumina, and Florisil. The obtained mixture was concentrated and subjected to ultrasonic cleaning using ethanol and recrystallization using toluene; thus, 4.66 g of the objective white solid was obtained in a yield of 63%.

Then, 3.83 g of the obtained white solid was purified by sublimation using a train sublimation method. In the purification by sublimation, the white solid was heated at 280° C. under a pressure of 2.7 Pa with a flow rate of argon of 5 mL/min After the purification by sublimation, 3.39 g of a white solid was obtained at a collection rate of 88.6%.

Figure 11A:
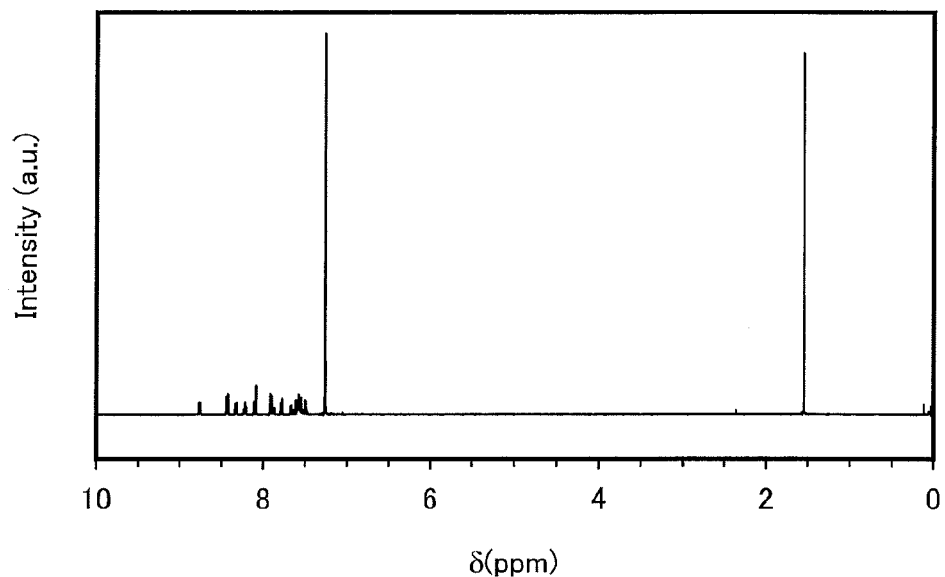
FIGS. 11A and 11B show $^1$H-NMR charts of a heterocyclic compound represented by Structural Formula (101).
Figure 11B:
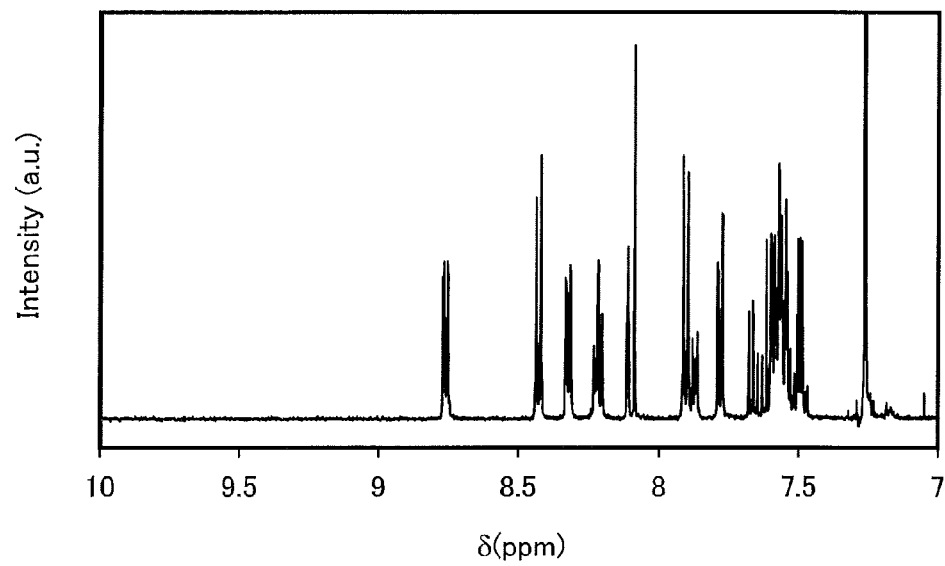

Results of analysis by nuclear magnetic resonance ($^1$H-NMR) spectroscopy of the compound obtained by the above-described synthesis method are described below. The $^1$H-NMR charts are shown in FIGS. 11A and 11B. The results reveal that 2,6Ph-4pmDBTBPPm-II (abbreviation), which is the heterocyclic compound of one embodiment of the present invention represented by Structural Formula (101), was obtained.

$^1$H NMR (CDCl$_3$, 500 MHz): δ=7.49-7.68 (m, 10H), 7.78 (dd, J=7.5 Hz, 2.0 Hz, 2H), 7.86-7.88 (m, 1H), 7.91 (d, J=8.5 Hz, 2H), 8.09 (s, 1H), 8.11 (t, J=1.7 Hz, 1H), 8.22 (m, 2H), 8.32 (dd, J=8.0 Hz, 2.0 Hz, 2H), 8.43 (d, J=8.5 Hz, 2H), 8.76 (dd, J=8.0 Hz, 2.0 Hz, 2H).

Next, 2,6Ph-4pmDBTBPPm-II (abbreviation) obtained in this example was analyzed by liquid chromatography mass spectrometry (LC/MS).

The analysis by LC/MS was carried out with Acquity UPLC (produced by Waters Corporation) and Xevo G2 T of MS (produced by Waters Corporation).

In the MS analysis, ionization was carried out by an electrospray ionization (ESI) method. Capillary voltage and sample cone voltage were set to 3.0 kV and 30 V, respectively. Detection was performed in a positive mode. A component which underwent the ionization under the above-mentioned conditions was collided with an argon gas in a collision cell to dissociate into product ions. Energy (collision energy) for the collision with argon was 70 eV. A mass range for the measurement was m/z=100-1200.

Figure 12:
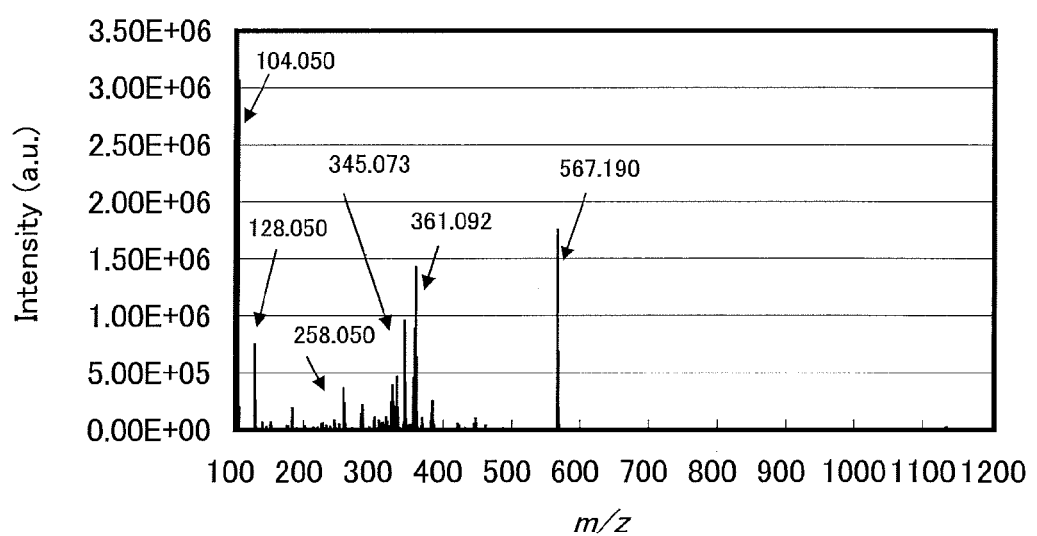
FIG. 12 shows results of LC-MS measurement of a heterocyclic compound represented by Structural Formula (101).

FIG. 12 shows the measurement results. The results in FIG. 12 show that as for 2,6Ph-4pmDBTBPPm-II (abbreviation), which is the heterocyclic compound of one embodiment of the present invention represented by Structural Formula (101), product ions are detected mainly around m/z=361, m/z=345, m/z=258, m/z=128, and m/z=104. Note that the results in FIG. 12 show characteristics derived from 2,6Ph-4pmDBTBPPm-II (abbreviation) and therefore can be regarded as important data for identifying 2,6Ph-4pmDBTBPPm-II (abbreviation) contained in a mixture.

It is probable that a C—C bond next to the nitrogen atom of the pyrimidine ring is cut, electric charge remains in a fragment containing the nitrogen atom, and the data appearing around m/z=361, m/z=128, and m/z=104 is thus data on a state where the C—C bond next to the nitrogen atom of the pyrimidine ring of the compound represented by Structural Formula (100) is cut; accordingly, the data is useful. In addition, the product ion around m/z=345 can be presumed to be a product ion including one dibenzothiophene ring and two benzene rings, and the product ion around m/z=258 can be presumed to be a product ion including one dibenzothiophene ring and one benzene ring; thus, it is suggested that 2,6Ph-4pmDBTBPPm-II (abbreviation), which is the heterocyclic compound of one embodiment of the present invention, includes a dibenzothiophene ring.

EXAMPLE 3

Figure 13:
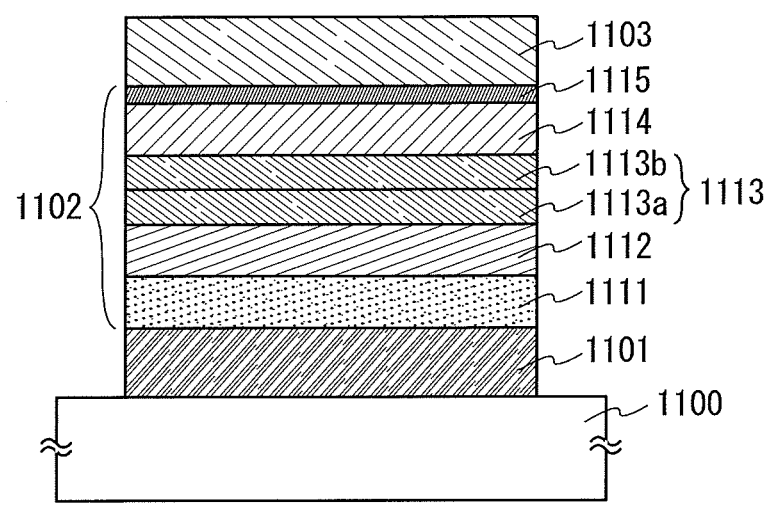
FIG. 13 illustrates a light-emitting element.

In this example, a light-emitting element 1 and a light-emitting element 2 each including a heterocyclic compound of one embodiment of the present invention in part of a light-emitting layer and an electron-transport layer will be described with reference to FIG. 13. The heterocyclic compounds included in the light-emitting element 1 and the light-emitting element 2 are 4-[3'-(4-dibenzothienyl)-1,1'-biphenyl-3-yl]-2,6-diphenylpyrimidine (abbreviation: 2,6Ph-4-mDBTBPPm-II) represented by Structural Formula (100) and 4-[3'-(4-dibenzothienyl)-1,1'-biphenyl-4-yl]-2,6-diphenylpyrimidine (abbreviation: 2,6Ph-4pmDBTBPPm-II) represented by Structural Formula (101), respectively. Chemical formulae of materials used in this example are shown below.

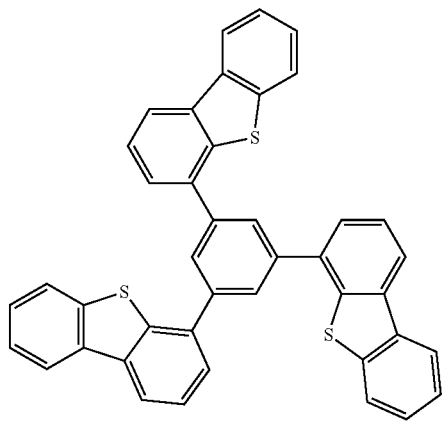

DBT3P-II

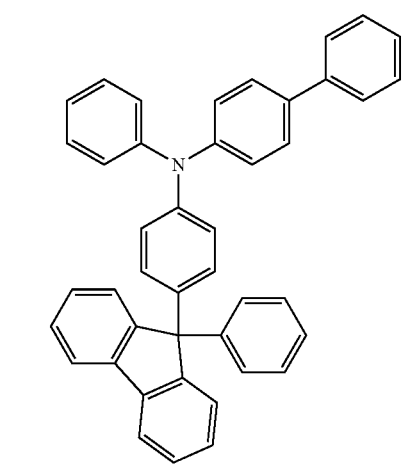

BFAFLP

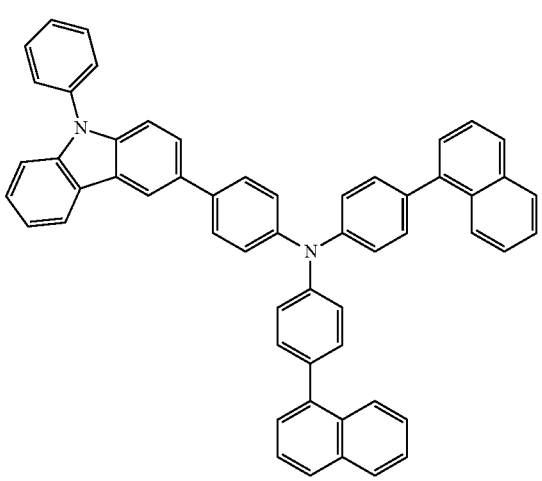

PCBNBB

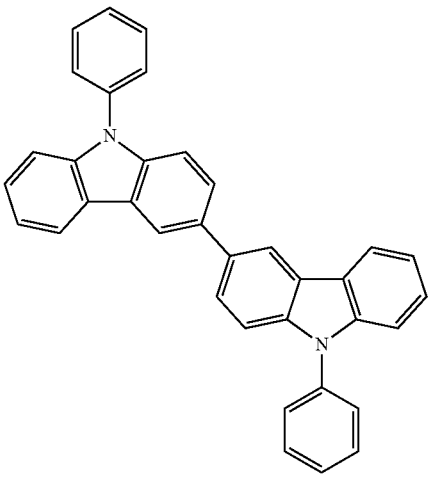

PCCP

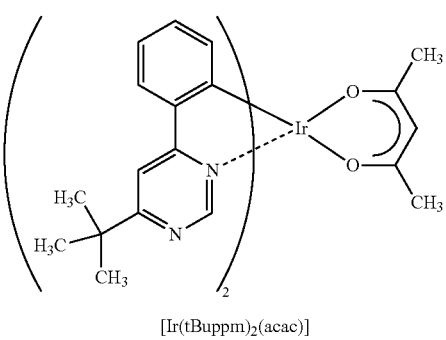

[Ir(tBuppm)$_2$(acac)]

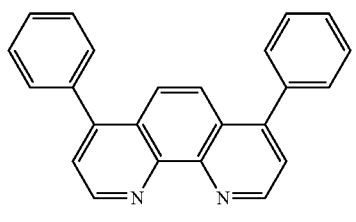

BPhen

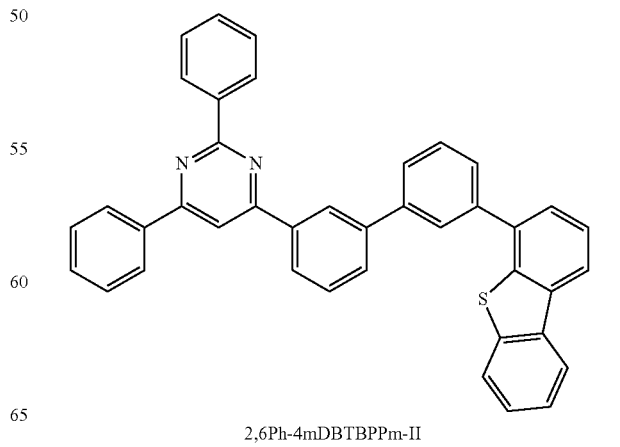

(100)

2,6Ph-4mDBTBPPm-II

-continued

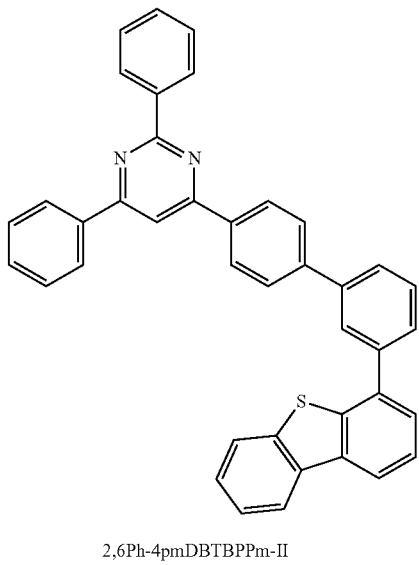

(101)

2,6Ph-4pmDBTBPPm-II

<<Fabrication of Light-Emitting Element 1 and Light-Emitting Element 2>>

First, indium tin oxide containing silicon oxide (ITSO) was deposited over a glass substrate 1100 by a sputtering method, so that a first electrode 1101 which functions as an anode was formed. The thickness was 110 nm and the electrode area was 2 mm×2 mm.

Next, as pretreatment for forming the light-emitting element over the substrate 1100, the surface of the substrate was washed with water, baked at 200° C. for 1 hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case is described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were deposited by co-evaporation with a mass ratio of 4:2 (=DBT3P-II (abbreviation): molybdenum oxide), so that the hole-injection layer 1111 was formed over the first electrode 1101. The thickness of the hole-injection layer 1111 was 40 nm. Note that co-evaporation is an evaporation method in which a plurality of different substances are concurrently vaporized from respective different evaporation sources.

Then, 4-phenyl-4'-(9-phenylfluoren-9-yl)triphenylamine (abbreviation: BPAFLP) and 3,3'-bis(9-phenyl-9H-carbazole) (abbreviation: PCCP) were deposited by co-evaporation with a mass ratio of BPAFLP (abbreviation) to PCCP (abbreviation) being 1:1, whereby the hole-transport layer 1112 was formed. The thickness was 20 nm.

Next, the light-emitting layer 1113 was formed over the hole-transport layer 1112.

In the light-emitting element 1, the light-emitting layer 1113 with a stacked-layer structure was formed to have a thickness of 40 nm by depositing 2,6Ph-4mDBTBPPm-II (abbreviation), 4,4'-di(1-naphthyl)-4"-(9-phenyl-9H-carbazol-3-yl)triphenylamine (abbreviation: PCBNBB), and (acetylacetonato)bis(6-tert-butyl-4-phenylpyrimidinato)iridium(III) (abbreviation: [Ir(tBuppm)$_2$(acac)]) by co-evaporation to a thickness of 20 nm with a mass ratio of 2,6Ph-4mDBTBPPm-II (abbreviation) to PCBNBB (abbreviation) and [Ir(tBuppm)$_2$(acac)] (abbreviation) being 0.5:0.5:0.05, and then depositing 2,6Ph-4mDBTBPPm-II (abbreviation), PCBNBB (abbreviation), and [Ir(tBuppm)$_2$(acac)] (abbreviation) to a thickness of 20 nm with a mass ratio of 2,6Ph-4mDBTBPPm-II (abbreviation) to PCBNBB (abbreviation) and [Ir(tBuppm)$_2$(acac)] (abbreviation) being 0.8:0.2:0.05.

In the light-emitting element 2, the light-emitting layer 1113 with a stacked-layer structure was formed to have a thickness of 40 nm by depositing 2,6Ph-4pmDBTBPPm-II (abbreviation), PCBNBB (abbreviation), and [Ir(tBuppm)$_2$(acac)] (abbreviation) by co-evaporation to a thickness of 20 nm with a mass ratio of 2,6Ph-4pmDBTBPPm-II (abbreviation) to PCBNBB (abbreviation) and [Ir(tBuppm)$_2$(acac)] (abbreviation) being 0.5:0.5:0.05, and then depositing 2,6Ph-4pmDBTBPPm-II (abbreviation), PCBNBB (abbreviation), and [Ir(tBuppm)$_2$(acac)] (abbreviation) to a thickness of 20 nm with a mass ratio of 2,6Ph-4pmDBTBPPm-II (abbreviation) to PCBNBB (abbreviation) and [Ir(tBuppm)$_2$(acac)] (abbreviation) being 0.8:0.2:0.05.

Note that in each of the light-emitting element 1 and the light-emitting element 2 in this example, exciplex formation in the light-emitting layer is possible.

Then, in the light-emitting element 1, 2,6Ph-4-mDBTB-PPm-II (abbreviation) was deposited by evaporation to a thickness of 10 nm over the light-emitting layer 1113 and bathophenanthroline (abbreviation: Bphen) was then deposited by evaporation to a thickness of 20 nm, whereby the electron-transport layer 1114 having a stacked-layer structure was formed. In the light-emitting element 2, 2,6Ph-4pmDBT-BPPm-II (abbreviation) was deposited by evaporation to a thickness of 10 nm over the light-emitting layer 1113 and bathophenanthroline (abbreviation: Bphen) was then deposited by evaporation to a thickness of 20 nm, whereby the electron-transport layer 1114 having a stacked-layer structure was formed.

Furthermore, lithium fluoride was deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form a second electrode 1103 serving as a cathode; thus, the light-emitting element 1 and the light-emitting element 2 were obtained. Note that in all the above evaporation steps, evaporation was performed by a resistance heating method.

Table 1 shows element structures of the light-emitting element 1 and the light-emitting element 2 obtained through the above-described steps.

TABLE 1

| | First electrode | Hole-injection Layer | Hole-transport Layer | Light-emitting Layer | | Electron-transport Layer | Electron-injection Layer | Second Electrode |
|---|---|---|---|---|---|---|---|---|
| Light-emitting Element 1 | ITSO (110 nm) | DBT3P-II: MoO$_x$ (4:2 40 nm) | BPAFLP: PCCP (1:1 20 nm) | * | ** | 2,6Ph-4mDBTBPPm-II (10 nm) | Bphen (20 nm) | LiF (1 nm) | Al (200 nm) |
| Light-emitting Element 2 | ITSO (110 nm) | DBT3P-II: MoO$_x$ (4:2 40 nm) | BPAFLP: PCCP (1:1 20 nm) | *** | **** | 2,6Ph-4pmDBTBPPm-II (10 nm) | Bphen (20 nm) | LiF (1 nm) | Al (200 nm) |

\* 2,6Ph-4mDBTBPPm-II:PCBNBB:[Ir(tBuppm)$_2$(acac)] (0.5:0.5:0.05 20 nm)
\*\* 2,6Ph-4mDBTBPPm-II:PCBNBB:[Ir(tBuppm)$_2$(acac)] (0.8:0.2:0.05 20 nm)
\*\*\* 2,6Ph-4pmDBTBPPm-II:PCBNBB:[Ir(tBuppm)$_2$(acac)] (0.5:0.5:0.05 20 nm)
\*\*\*\* 2,6Ph-4pmDBTBPPm-II:PCBNBB:[Ir(tBuppm)$_2$(acac)] (0.8:0.2:0.05 20 nm)

Further, the fabricated light-emitting elements 1 and 2 were sealed in a glove box containing a nitrogen atmosphere so as not to be exposed to the air (specifically, a sealant was applied onto an outer edge of the element and heat treatment was performed at 80° C. for 1 hour at the time of sealing).

<<Operation Characteristics of Light-Emitting Element 1 and Light-Emitting Element 2>>

Operation characteristics of the fabricated light-emitting elements 1 and 2 were measured. Note that the measurement was carried out at room temperature (in an atmosphere kept at 25° C.).

Figure 14:
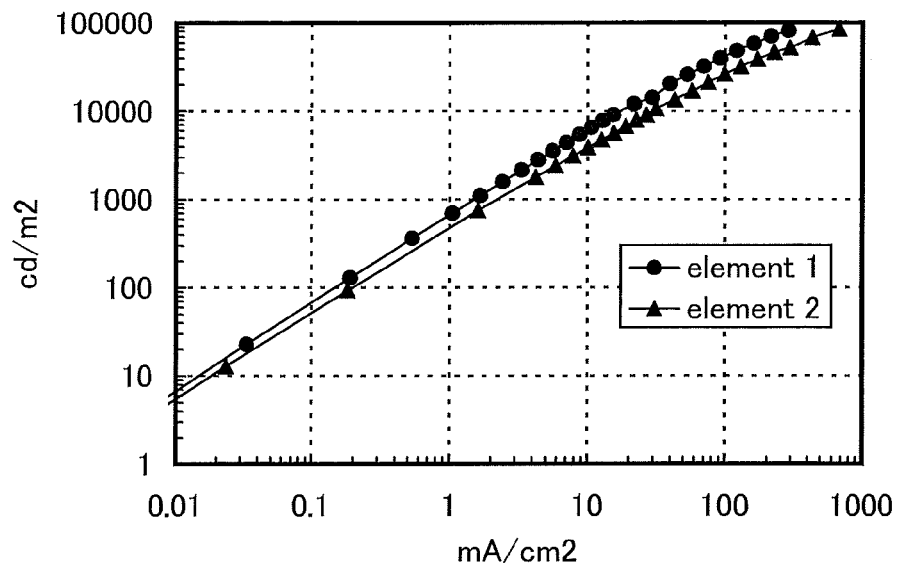
FIG. 14 shows current density-luminance characteristics of a light-emitting element 1 and a light-emitting element 2.
Figure 15:
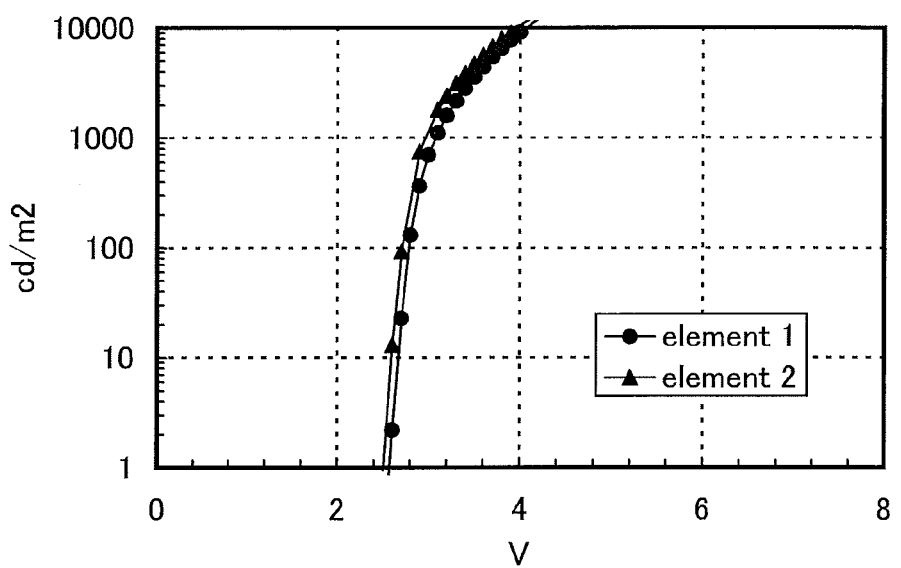
FIG. 15 shows voltage-luminance characteristics of a light-emitting element 1 and a light-emitting element 2.
Figure 16:
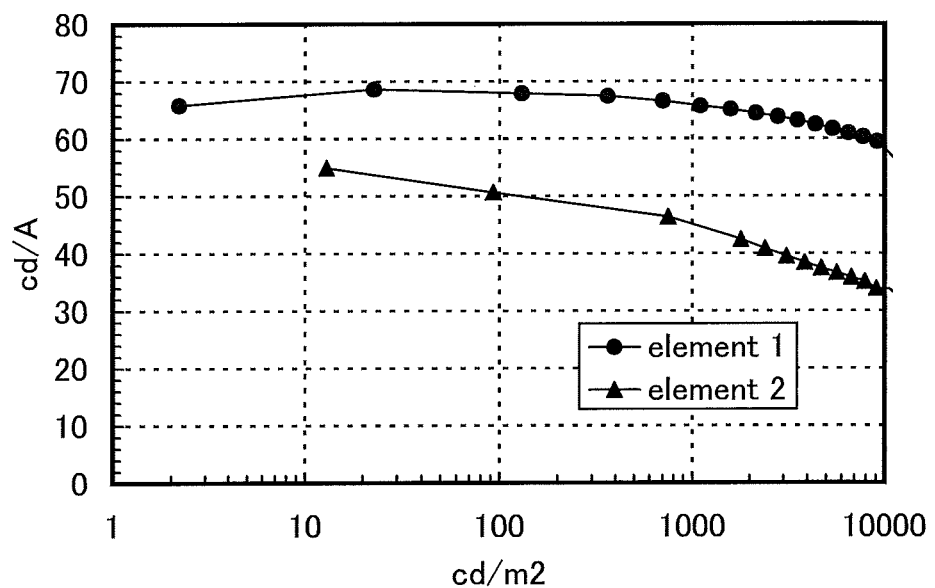
FIG. 16 shows luminance-current efficiency characteristics of a light-emitting element 1 and a light-emitting element 2.
Figure 17:
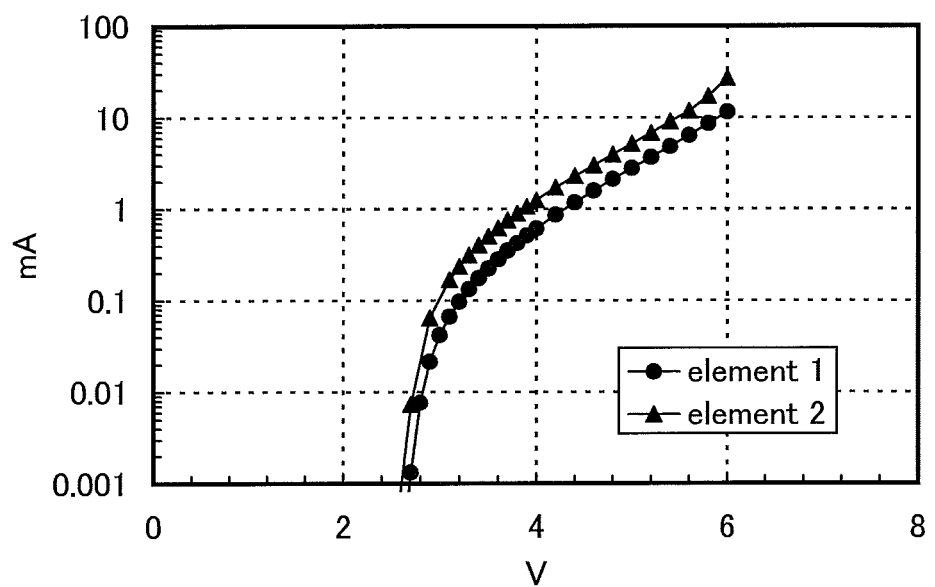
FIG. 17 shows voltage-current characteristics of a light-emitting element 1 and a light-emitting element 2.

FIG. 14 shows current density-luminance characteristics of the light-emitting elements 1 and 2, FIG. 15 shows voltage-luminance characteristics thereof, FIG. 16 shows luminance-current efficiency characteristics thereof, and FIG. 17 shows voltage-current characteristics thereof.

FIG. 16 reveals that the light-emitting element 1 and the light-emitting element 2, which use the heterocyclic compounds of embodiments of the present invention in the light-emitting layers and the electron-transport layers, have reduced power consumption and high efficiency.

Table 2 shows initial values of main characteristics of the light-emitting elements 1 and 2 at a luminance of about 1000 cd/m$^2$.

The above results in Table 2 also show that the light-emitting elements 1 and 2 fabricated in this example have high luminance and high current efficiency.

Figure 18:
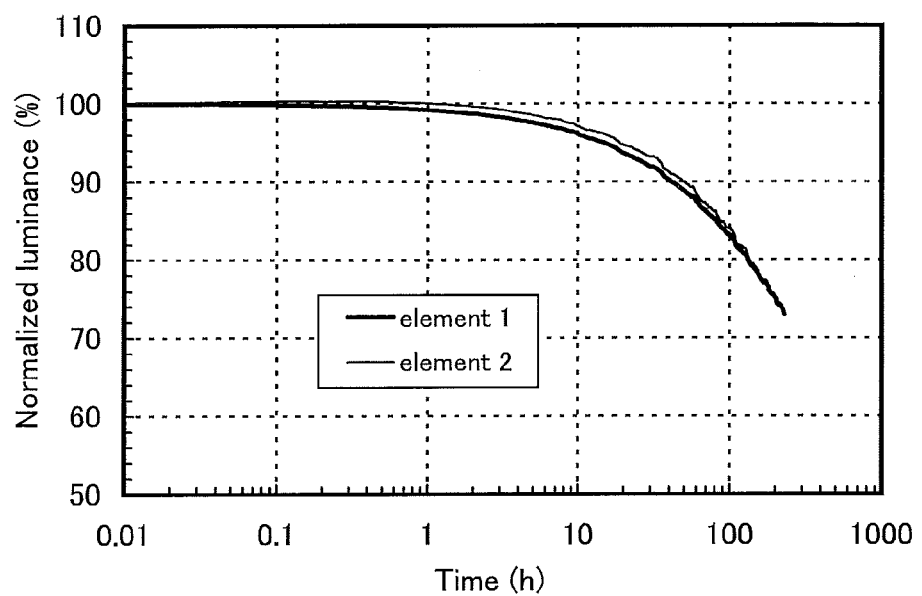
FIG. 18 shows reliability of a light-emitting element 1 and a light-emitting element 2.

The light-emitting elements 1 and 2 were subjected to reliability tests. FIG. 18 shows results of the reliability tests.

In FIG. 18, the vertical axis indicates normalized luminance (%) with an initial luminance of 100% and the horizontal axis indicates driving time (h) of the element. Note that in the reliability tests, the light-emitting elements 1 and 2 were driven under the conditions where the initial luminance was set to 5000 cd/m$^2$ and the current density was constant. The light-emitting elements 1 and 2 kept about 83% of the initial luminance after 100 hours elapsed.

The results of the reliability tests showed that the light-emitting element 1 and the light-emitting element 2 have high reliability. In addition, it was confirmed that with the use of the heterocyclic compound that is one embodiment of the present invention, a light-emitting element with a long lifetime can be obtained.

EXAMPLE 4

Synthesis Example 3

In this example, a method for synthesizing 4-[3'-(dibenzothiophen-4-yl)-1,1'-biphenyl-3-yl]-6-phenylpyrimidine (abbreviation: 6Ph-4mDBTBPPm-II), which is the heterocyclic compound of one embodiment of the present invention

TABLE 2

| | Voltage (V) | Current (mA) | Current Density (mA/cm$^2$) | Chromaticity (x, y) | Luminance (cd/m$^2$) | Current Efficiency (cd/A) | Power Efficiency (lm/W) | External Quantum Efficiency (%) |
|---|---|---|---|---|---|---|---|---|
| Light-emitting Element 1 | 3.1 | 0.067 | 1.7 | (0.42, 0.56) | 1100 | 66 | 67 | 18 |
| Light-emitting Element 2 | 2.9 | 0.064 | 1.6 | (0.41, 0.57) | 750 | 46 | 50 | 13 | represented by Structural Formula (112) in Embodiment 1, will be described. A structure of 6Ph-4mDBTBPPm-II (abbreviation) is shown below.

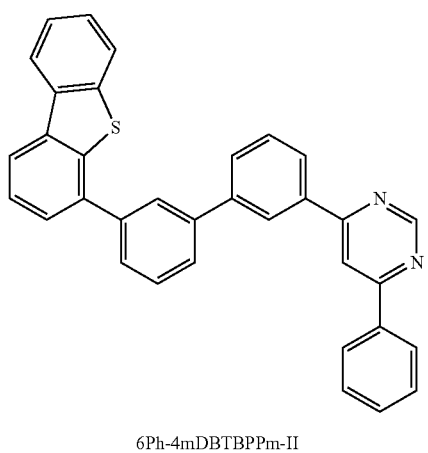

6Ph-4mDBTBPPm-II (112)

Step 1: Synthesis of 4-Chloro-6-phenylpyrimidine

Into a 100-mL round-bottom flask equipped with a reflux pipe were put 5.1 g of 4,6-dichloropyrimidine, 8.2 g of phenylboronic acid, 7.16 g of sodium carbonate, 20 mL of acetonitrile, and 20 mL of water, and the air in the flask was replaced with nitrogen. To this mixture, 0.347 g of bis(triphenylphosphine)palladium(II) dichloride was added and the mixture was irradiated with microwaves (2.45 GHz, 100 W) for 1 hour. Further, 2.07 g of phenylboronic acid and 1.79 g of sodium carbonate were added and the mixture was irradiated with microwaves (2.45 GHz, 100 W) for 1 hour. An organic layer was extracted from the obtained mixture with the use of dichloromethane. The obtained organic layer was washed with water and a saturated aqueous solution of sodium chloride and dried over magnesium sulfate. The mixture was subjected to gravity filtration. A residue obtained by distilling off the solvent in the filtrate was purified by silica column chromatography with the use of dichloromethane as a developing solvent to give an objective substance as a white powder in a yield of 37%. Note that the irradiation with microwaves was performed using a microwave synthesis system (Discover, manufactured by CEM Corporation). Synthesis Scheme (D-1) of Step 1 is shown below.

Step 2: Synthesis of 4-[3'-(Dibenzothiophen-4-yl)-1,1'-biphenyl-3-yl]-6-phenylpyrimidine (abbreviation: 6Ph-4mDBTBPPm-II)

Then, 1.0 g of 4-chloro-6-phenylpyrimidine obtained in Step 1, 2.0 g of 3'-(dibenzothiophen-4-yl)-3-biphenylboronic acid, 5.3 mL of a 2M aqueous solution of potassium carbonate, 24 mL of toluene, and 3.0 mL of ethanol were put into a 100-mL three-neck flask equipped with a reflux pipe. Degasification by stirring under a reduced pressure was performed and the air in the flask was replaced with nitrogen. To this mixture, 61 mg of tetrakis(triphenylphosphine)palladium(0) (abbreviation: Pd(PPh$_3$)$_4$) was added and the mixture was heated at 80° C. for 7 hours to cause a reaction. An organic layer was extracted from the obtained mixture with the use of toluene and was washed with water and a saturated aqueous solution of sodium chloride. Anhydrous magnesium sulfate was added and gravity filtration was performed. After the solvent in this solution was distilled off, the obtained residue was dissolved in hot toluene and subjected to hot filtration through a filter aid in which Celite, alumina, Celite, Florisil, and Celite were stacked in this order. The solvent was distilled off and the obtained solid was recrystallized with toluene, so that 1.9 g of a white solid was obtained in a yield of 71%. Synthesis Scheme (D-2) of Step 2 is shown below.

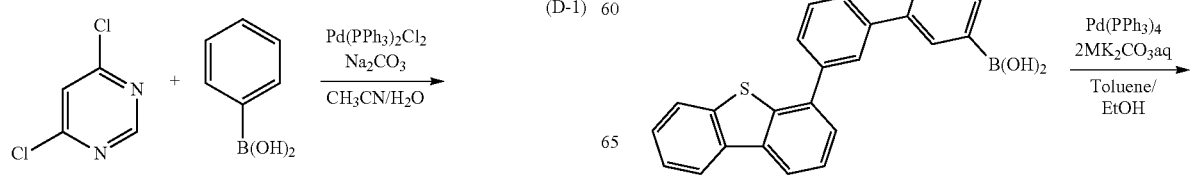

(D-1)

(D-2)

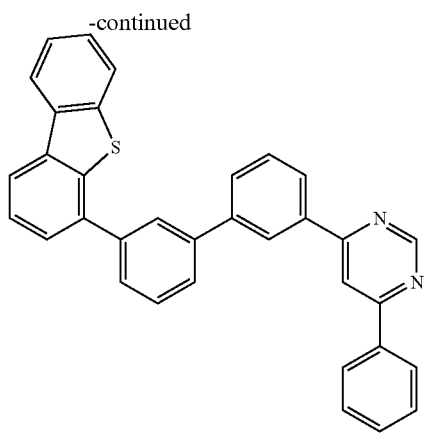

6Ph-4mDBTBPPm-II
(112)

Then, 2.4 g of the obtained solid was purified by sublimation using a train sublimation method. Conditions for the purification by sublimation were set as follows: the pressure was 3.0 Pa, the flow rate of argon gas was 15 mL/min, and the heating temperature was 265° C. After the purification by sublimation, 1.9 g of colorless transparent crystals of the objective substance were obtained at a collection rate of 79%.

Figure 19:
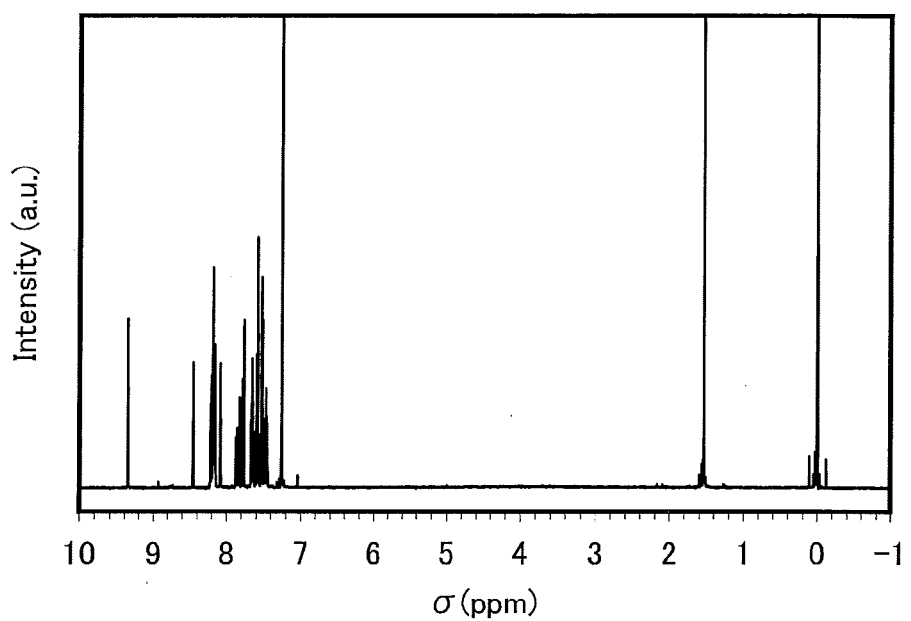
FIG. 19 shows a $^1$H-NMR chart of a heterocyclic compound represented by Structural Formula (112).

Results of analysis by nuclear magnetic resonance ($^1$H-NMR) spectroscopy of the white solid obtained in Step 2 are described below. The $^1$H-NMR chart is shown in FIG. 19. The results reveal that 6Ph-4mDBTBPPm-II (abbreviation), which is the heterocyclic compound of one embodiment of the present invention represented by Structural Formula (112), was obtained.

$^1$H-NMR. δ(CDCl$_3$): 7.45-7.50 (dm, 2H), 7.52-7.54 (m, 3H), 7.56-7.61 (m, 2H), 7.63-7.67 (m, 2H), 7.76-7.77 (ds, 1H), 7.78 (ds, 1H), 7.82-7.83 (dd, 1H), 7.85-7.87 (dd, 1H), 8.08-8.09 (ts, 1H), 8.14-8.22 (dm, 6H), 8.45-8.46 (ts, 1H), 9.34-9.35 (ds, 1H).

Next, 6Ph-4mDBTBPPm-II (abbreviation) was analyzed by liquid chromatography mass spectrometry (LC/MS).

The analysis by LC/MS was carried out with Acquity UPLC (produced by Waters Corporation) and Xevo G2 T of MS (produced by Waters Corporation).

In the MS analysis, ionization was carried out by an electrospray ionization (ESI) method. Capillary voltage and sample cone voltage were set to 3.0 kV and 30 V, respectively. Detection was performed in a positive mode. A component which underwent the ionization under the above-mentioned conditions was collided with an argon gas in a collision cell to dissociate into product ions. Energy (collision energy) for the collision with argon was 50 eV and 70 eV. A mass range for the measurement was m/z=100-1200.

Figure 20:
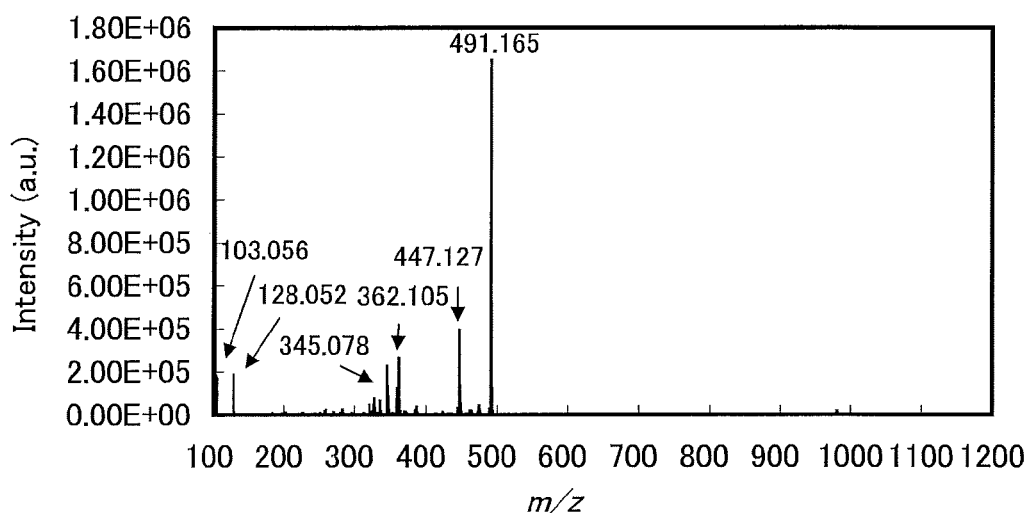
FIG. 20 shows results of LC-MS measurement of a heterocyclic compound represented by Structural Formula (112).
Figure 21:
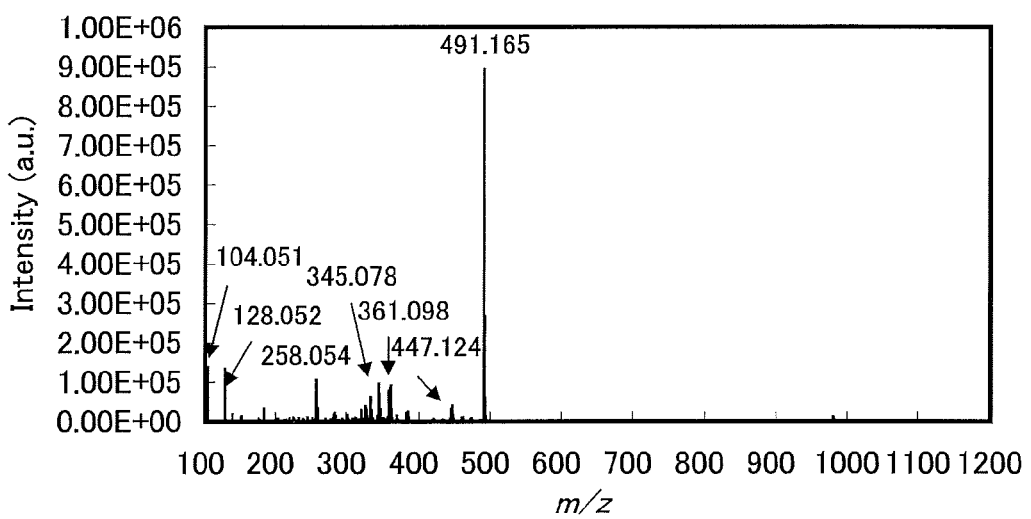
FIG. 21 shows results of LC-MS measurement of a heterocyclic compound represented by Structural Formula (112).

FIG. 20 and FIG. 21 show the measurement results. FIG. 20 shows the results at the time when the collision energy was 50 eV. FIG. 21 shows the results at the time when the collision energy was 70 eV. The results in FIG. 20 and FIG. 21 show that as for 6Ph-4mDBTBPPm-II (abbreviation), which is the heterocyclic compound of one embodiment of the present invention represented by Structural Formula (112), product ions are detected mainly around m/z=447, m/z=361, m/z=345, m/z=258, m/z=128, and m/z=104. Note that the results in FIG. 20 and FIG. 21 show characteristics derived from 6Ph-4mDBTBPPm-II (abbreviation) and therefore can be regarded as important data for identifying 6Ph-4mDBTBPPm-II (abbreviation) contained in a mixture.

It is probable that a C—C bond next to the nitrogen atom of the pyrimidine ring is cut, electric charge remains in a fragment containing the nitrogen atom, and the data appearing around m/z=361, m/z=128, and m/z=104 is thus data on a state where the C—C bond next to the nitrogen atom of the pyrimidine ring of the compound represented by Structural Formula (112) is cut; accordingly, the data is useful. In addition, the product ion around m/z=345 can be presumed to be a product ion including one dibenzothiophene ring and two benzene rings, and the product ion around m/z=258 can be presumed to be a product ion including one dibenzothiophene ring and one benzene ring; thus, it is suggested that 6Ph-4mDBTBPPm-II (abbreviation), which is the heterocyclic compound of one embodiment of the present invention, includes a dibenzothiophene ring.

EXAMPLE 5

Synthesis Example 4

In this example, a method for synthesizing 4-[3'-(dibenzothiophen-4-yl)-1,1'-biphenyl-3-yl]-6-(9,9-dimethylfluoren-2-yl)pyrimidin e (abbreviation: 6FL-4mDBTBPPm), which is one embodiment of the present invention represented by Structural Formula (121) in Embodiment 1, will be described. A structure of 6FL-4mDBTBPPm (abbreviation) is shown below.

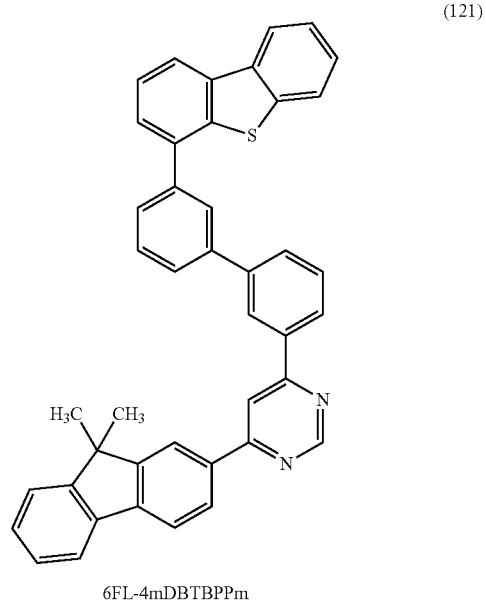 [SMILES: CC1(C)c2ccccc2-c2ccc(-c3cc(-c4cccc(-c5cccc(-c6cccc7c6sc6ccccc67)c5)c4)ncn3)cc21]

(121)

6FL-4mDBTBPPm

Step 1: Synthesis of 4-Chloro-6-[3-(3'-dibenzothiophen-4-yl)biphenyl]pyrimidine

First, 0.20 g (1.3 mmol) of 4,6-dichloropyrimidine, 0.51 g (1.3 mmol) of 3'-(dibenzothiophen-4-yl)-3-biphenylboronic acid, 0.85 g (2.6 mmol) of cesium carbonate, 0.2 mL (0.83 mmol) of tricyclohexylphosphine (Cy$_3$P), 18 mg (0.020 mmol) of tris(dibenzylideneacetone)palladium(0) (Pd$_2$(dba)$_3$), and 10 mL of dioxane were put into a 100-mL round-bottom flask, the mixture was bubbled with argon for 15 minutes and irradiated with microwaves (85° C., 150 W) for 2 hours. An aqueous layer of the obtained solution was extracted with dichloromethane. The obtained solution of the extract and the organic layer were combined and washed with water and a saturated aqueous solution of sodium chloride, and anhydrous magnesium sulfate was added to the organic layer for drying. This mixture was subjected to gravity filtration, and the filtrate was concentrated to give a solid. This solid was purified by flash column chromatography using dichloromethane as a developing solvent. Purification by silica gel column chromatography using toluene as a developing solvent was further performed. A solid obtained by concentration of the obtained fraction was recrystallized with toluene, so that 4-chloro-6-[3-(3'-dibenzothiophen-4-yl)biphenyl]pyrimidine was obtained as a white solid in a yield of 44%. Synthesis Scheme (E-1) of Step 1 is shown below.

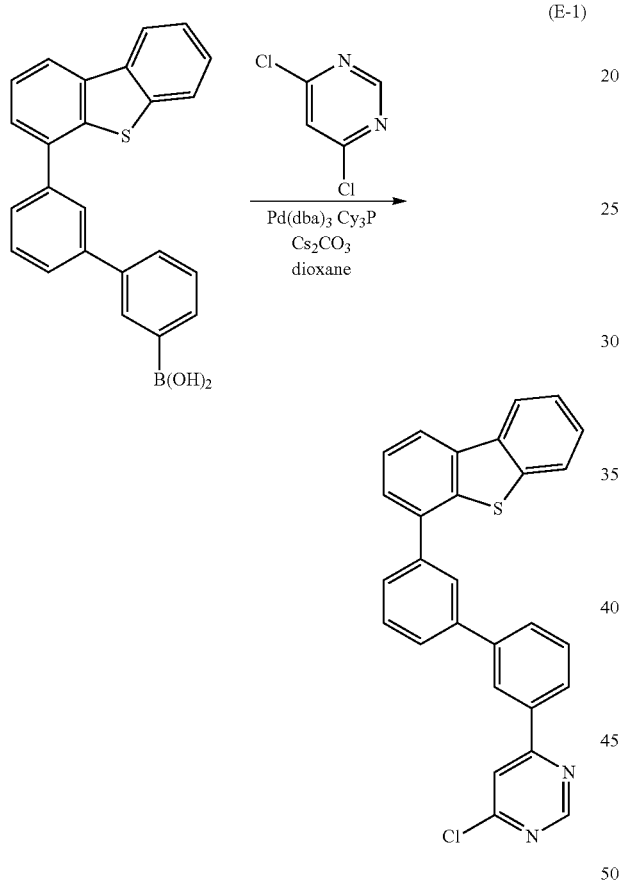

(E-1)

Step 2: Synthesis of 4-[3'-(Dibenzothiophen-4-yl)-1,1'-biphenyl-3-yl]-6-(9,9-dimethylfluoren-2-yl)pyrimidine (abbreviation: 6FL-4mDBTBPPm)

Then, 1.0 g (2.6 mmol) of 4-chloro-6-[3-(3'-dibenzothiophen-4-yl)biphenyl]pyrimidine, 1.0 g (3.2 mmol) of 9,9-dimethylfluorene-2-boronic acid pinacol ester, 15 mL of toluene, 3 mL of ethanol, and 2.6 mL of a 2M aqueous solution of potassium carbonate were put into a 200-mL reaction container, and the air in the container was replaced with nitrogen. To this mixture, 30 mg (0.02 mmol) of tetrakis(triphenylphosphine)palladium(0) (Pd(PPh$_3$)$_4$) was added and the mixture was heated and stirred at 80° C. for 8 hours. The aqueous layer of the obtained reacted solution was subjected to extraction with toluene, and the obtained solution of the extract and the organic layer were combined and washed with water and a saturated aqueous solution of sodium chloride. Anhydrous magnesium sulfate was added to the organic layer for drying, and the resulting mixture was subjected to gravity filtration to give a filtrate. A solid which was obtained by concentration of this filtrate was purified by silica gel column chromatography. Toluene was used as a developing solvent. The obtained fraction was concentrated to give a solid. This solid was recrystallized with ethanol, so that 6FL-4mDBTBPPm was obtained as a white solid in a yield of 51%. Synthesis Scheme (E-2) of Step 2 is shown below.

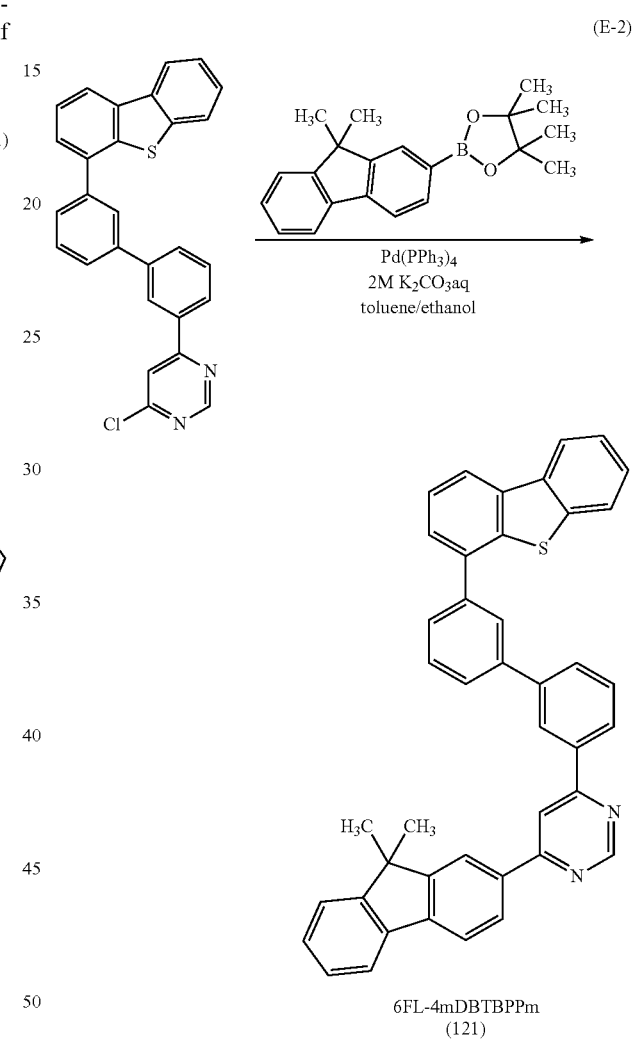

(E-2)

Then, 0.81 g of the obtained solid was purified by sublimation using a train sublimation method. Conditions for the purification by sublimation were set as follows: the pressure was 2.6 Pa, the flow rate of argon gas was 10 mL/min, and the heating temperature was 270° C. After the purification by sublimation, 0.47 g of pale yellow transparent crystals of the objective substance were obtained at a collection rate of 58%.

Figure 22:
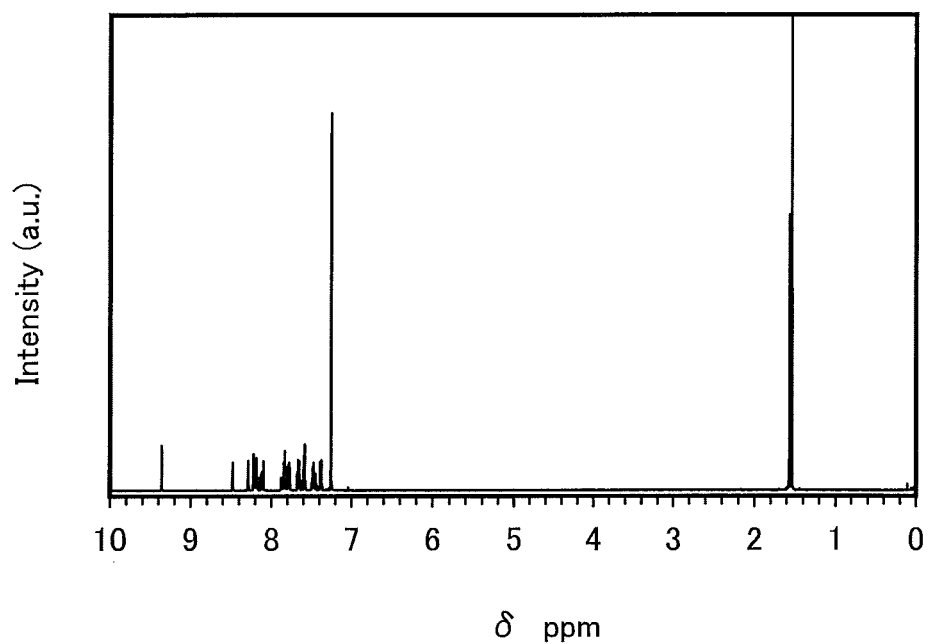
FIG. 22 shows a $^1$H-NMR chart of a heterocyclic compound represented by Structural Formula (121).

Results of analysis by nuclear magnetic resonance ($^1$H-NMR) spectroscopy of the white solid obtained in Step 2 are described below. The $^1$H-NMR chart is shown in FIG. 22. The results reveal that 6FL-4mDBTBPPm (abbreviation), which is the heterocyclic compound of one embodiment of the present invention represented by Structural Formula (121), was obtained in Synthesis Example 4.

$^1$H-NMR. δ(CDCl$_3$): 1.58 (s, 6H), 7.36-7.39 (m, 2H), 7.43-7.50 (m, 3H), 7.57-7.61 (m, 2H), 7.77-7.80 (m, m), 7.85 (dd, 2H), 7.88 (d, 1H), 8.11 (t, 1H), 8.14 (dd, 1H), 8.17-8.23 (m, 4H), 8.29 (d, 1H), 8.49 (t, 1H), 9.37 (d, 1H).

Next, 6FL-4mDBTBPPm (abbreviation) was analyzed by liquid chromatography mass spectrometry (LC/MS).

The analysis by LC/MS was carried out with Acquity UPLC (produced by Waters Corporation) and Xevo G2 T of MS (produced by Waters Corporation).

In the MS analysis, ionization was carried out by an electrospray ionization (ESI) method. Capillary voltage and sample cone voltage were set to 3.0 kV and 30 V, respectively. Detection was performed in a positive mode. A component which underwent the ionization under the above-mentioned conditions was collided with an argon gas in a collision cell to dissociate into product ions. Energy (collision energy) for the collision with argon was 70 eV. A mass range for the measurement was m/z=100-1200.

Figure 23:
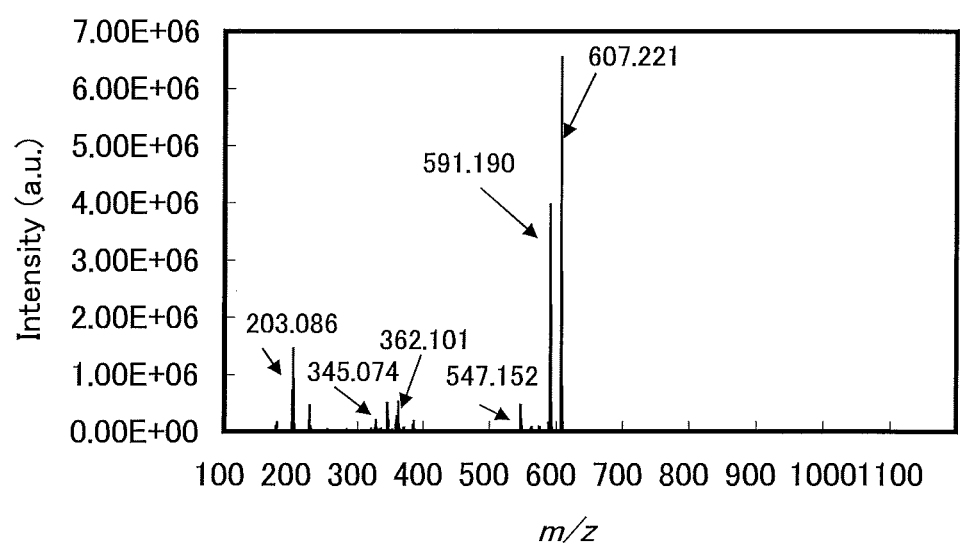
FIG. 23 shows results of LC-MS measurement of a heterocyclic compound represented by Structural Formula (121).

FIG. 23 shows the measurement results. The results in FIG. 23 show that as for 6FL-4mDBTBPPm (abbreviation), which is the heterocyclic compound of one embodiment of the present invention represented by Structural Formula (121), product ions are detected mainly around m/z=591, m/z=547, m/z=362, m/z=345, and m/z=203. Note that the results in FIG. 23 show characteristics derived from 6FL-4mDBTB-PPm (abbreviation) and therefore can be regarded as important data for identifying 6FL-4mDBTBPPm (abbreviation) contained in a mixture.

It is probable that a C—C bond next to the nitrogen atom of the pyrimidine ring is cut, electric charge remains in a fragment containing the nitrogen atom, and the data appearing around m/z=362 is thus data on a state where the C—C bond next to the nitrogen atom of the pyrimidine ring of the compound represented by Structural Formula (121) is cut; accordingly, the data is useful. In addition, the product ion around m/z=345 can be presumed to be a product ion including one dibenzothiophene ring and two benzene rings; thus, it is suggested that 6FL-4mDBTBPPm (abbreviation), which is the heterocyclic compound of one embodiment of the present invention, includes a dibenzothiophene ring.

EXAMPLE 6

In this example, a light-emitting element 3 and a light-emitting element 4 each including a heterocyclic compound of one embodiment of the present invention in part of a light-emitting layer and an electron-transport layer will be similarly described with reference to FIG. 13 used in Example 3. The heterocyclic compounds included in the light-emitting element 3 and the light-emitting element 4 are 4-[3'-(dibenzothiophen-4-yl)-1,1'-biphenyl-3-yl]-6-phenylpyrimidine (abbreviation: 6Ph-4mDBTBPPm-II) represented by Structural Formula (112) and 4-[3'-(dibenzothiophen-4-yl)-1,1'-biphenyl-3-yl]-6-(9,9-dimethylfluoren-2-yl)pyrimidin e (abbreviation: 6FL-4mDBTBPPm) represented by Structural Formula (121), respectively. Chemical formulae of materials used in this example are shown below.

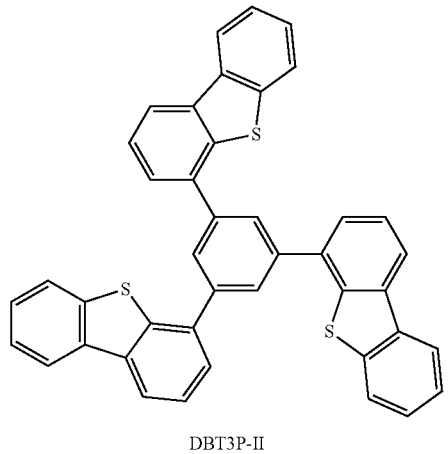

DBT3P-II

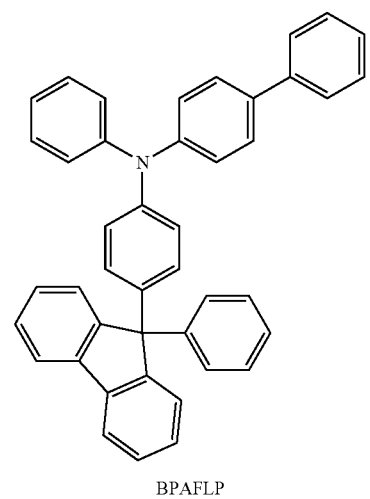

BPAFLP

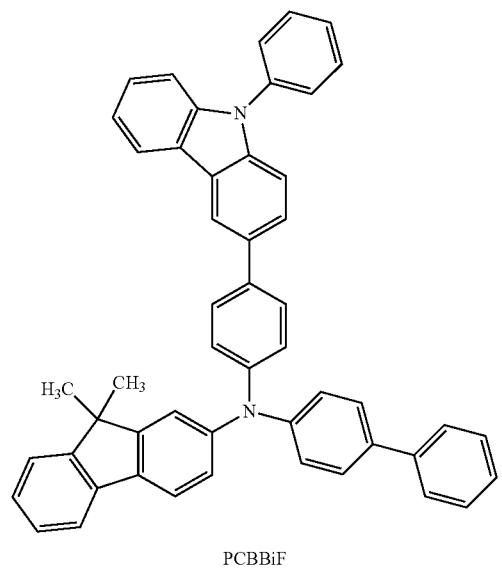

PCBBiF

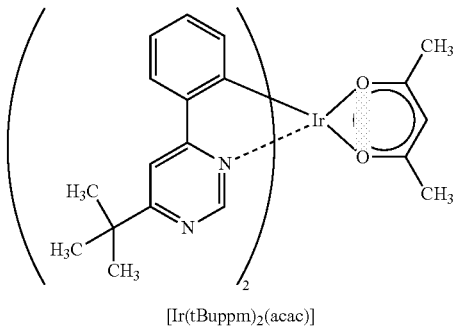

[Ir(tBuppm)₂(acac)]

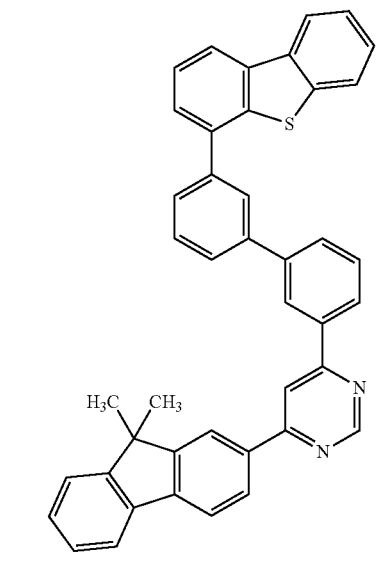

6FL-4mDBTBPPm

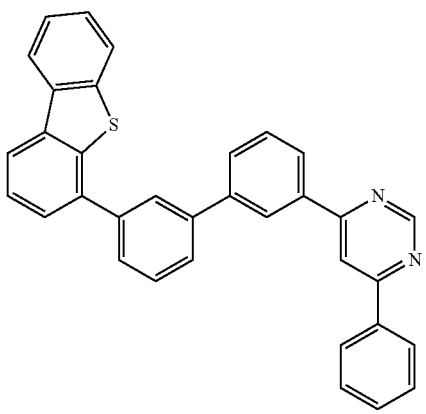

6Ph-4mDBTBPPm-II

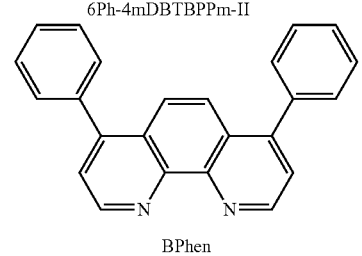

BPhen

<<Fabrication of Light-Emitting Element 3 and Light-Emitting Element 4>>

First, indium tin oxide containing silicon oxide (ITSO) was deposited over the glass substrate 1100 by a sputtering method, so that the first electrode 1101 which functions as an anode was formed. The thickness was 110 nm and the electrode area was 2 mm×2 mm.

Next, as pretreatment for forming the light-emitting element over the substrate 1100, the surface of the substrate was washed with water, baked at 200° C. for 1 hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case is described in which the hole-injection layer 1111, the hole-transport layer 1112, the light-emitting layer 1113, the electron-transport layer 1114, and the electron-injection layer 1115 which are included in the EL layer 1102 are sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were deposited by co-evaporation with a mass ratio of 4:2 (=DBT3P-II (abbreviation): molybdenum oxide), so that the hole-injection layer 1111 was formed over the first electrode 1101. The thickness of the hole-injection layer 1111 was 20 nm. Note that co-evaporation is an evaporation method in which a plurality of different substances are concurrently vaporized from respective different evaporation sources.

Then, 4-phenyl-4'-(9-phenylfluoren-9-yl)triphenylamine (abbreviation: BPAFLP) was deposited by evaporation, whereby the hole-transport layer 1112 was formed. The thickness was 20 nm.

Next, the light-emitting layer 1113 was formed over the hole-transport layer 1112.

In the light-emitting element 3, the light-emitting layer 1113 with a stacked-layer structure was formed to have a thickness of 40 nm by depositing 6Ph-4mDBTBPPm-II (abbreviation), N-(1,1'-biphenyl-4-yl)-N-[4-(9-phenyl-9H-carbazol-3-yl)phenyl]-9,9-dimethyl-9H-fluor en-2-amine (abbreviation: PCBBiF), and (acetylacetonato)bis(6-tert-butyl-4-phenylpyrimidinato)iridium(III) (abbreviation: [Ir(tBuppm)₂(acac)]) by co-evaporation to a thickness of 20 nm with a mass ratio of 6Ph-4mDBTBPPm-II (abbreviation) to PCBBiF (abbreviation) and [Ir(tBuppm)₂(acac)] (abbreviation) being 0.7:0.3:0.05, and then depositing 6Ph-4mDBTB-PPm-II (abbreviation), PCBBiF (abbreviation), and [Ir(tBuppm)₂(acac)] (abbreviation) to a thickness of 20 nm with a mass ratio of 6Ph-4mDBTBPPm-II (abbreviation) to PCBBiF (abbreviation) and [Ir(tBuppm)₂(acac)] (abbreviation) being 0.8:0.2:0.05.

In the light-emitting element 4, the light-emitting layer 1113 with a stacked-layer structure was faulted to have a thickness of 40 nm by depositing 6FL-4mDBTBPPm (abbreviation), PCBBiF (abbreviation), and [Ir(tBuppm)₂(acac)] (abbreviation) by co-evaporation to a thickness of 20 nm with a mass ratio of 6FL-4mDBTBPPm (abbreviation) to PCBBiF (abbreviation) and [Ir(tBuppm)₂(acac)] (abbreviation) being 0.7:0.3:0.05, and then depositing 6FL-4mDBTBPPm (abbreviation), PCBBiF (abbreviation), and [Ir(tBuppm)₂(acac)]

(abbreviation) to a thickness of 20 nm with a mass ratio of 6FL-4mDBTBPPm (abbreviation) to PCBBiF (abbreviation) and [Ir(tBuppm)$_2$(acac)] (abbreviation) being 0.8:0.2:0.05.

Note that in each of the light-emitting element 3 and the light-emitting element 4 in this example, exciplex formation in the light-emitting layer is possible.

Then, in the light-emitting element 3, 6Ph-4mDBTBPPm-II (abbreviation) was deposited by evaporation to a thickness of 15 nm over the light-emitting layer 1113 and bathophenanthroline (abbreviation: Bphen) was then deposited by evaporation to a thickness of 15 nm, whereby the electron-transport layer 1114 having a stacked-layer structure was formed. In the light-emitting element 4, 6FL-4mDBTBPPm (abbreviation) was deposited by evaporation to a thickness of 15 nm over the light-emitting layer 1113 and bathophenanthroline (abbreviation: Bphen) was then deposited by evaporation to a thickness of 10 nm, whereby the electron-transport layer 1114 having a stacked-layer structure was formed.

Furthermore, lithium fluoride was deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form the second electrode 1103 serving as a cathode; thus, the light-emitting element 3 and the light-emitting element 4 were obtained. Note that in all the above evaporation steps, evaporation was performed by a resistance heating method.

Table 3 shows element structures of the light-emitting element 3 and the light-emitting element 4 obtained through the above-described steps.

<<Operation Characteristics of Light-Emitting Element 3 and Light-Emitting Element 4>>

Operation characteristics of the fabricated light-emitting elements 3 and 4 were measured. Note that the measurement was carried out at room temperature (in an atmosphere kept at 25° C.).

Figure 24:
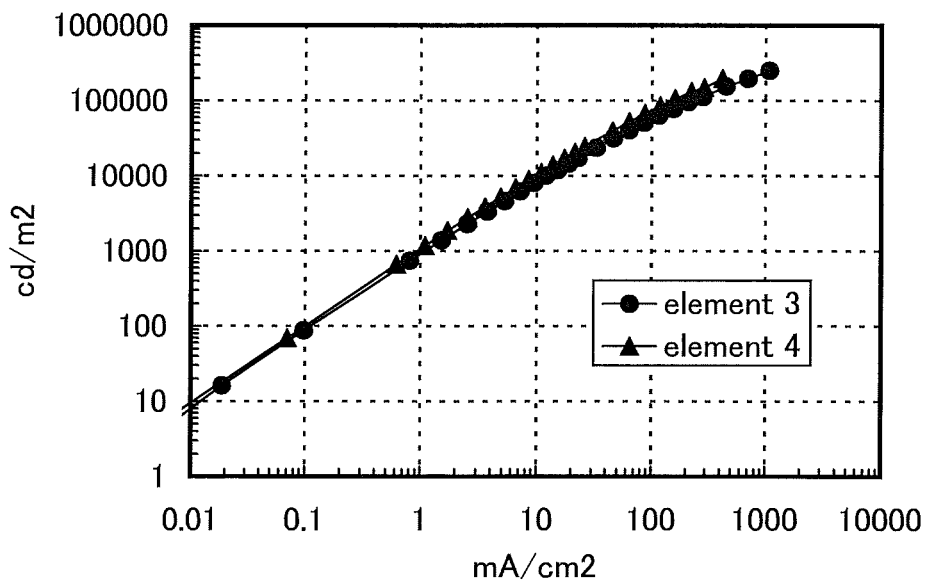
FIG. 24 shows current density-luminance characteristics of a light-emitting element 3 and a light-emitting element 4.
Figure 25:
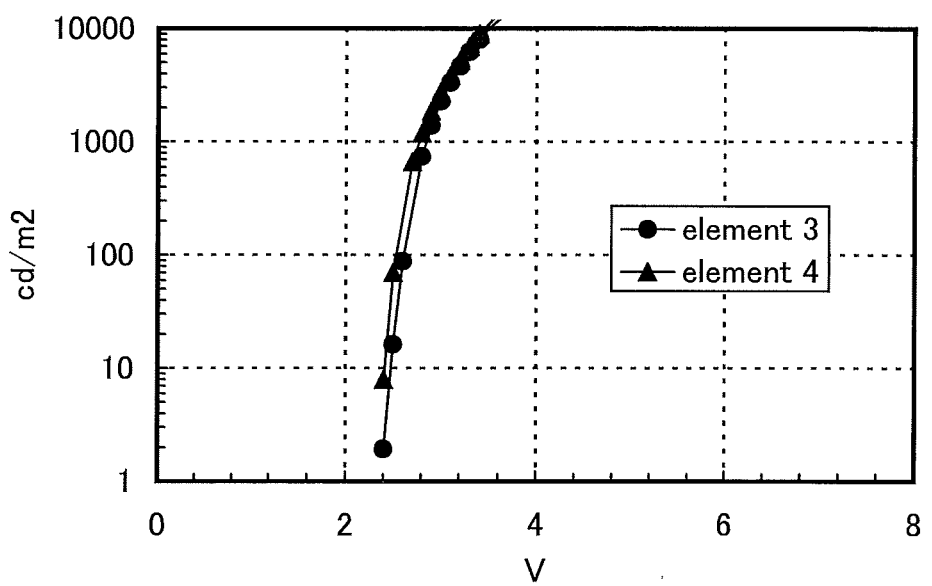
FIG. 25 shows voltage-luminance characteristics of a light-emitting element 3 and a light-emitting element 4.
Figure 26:
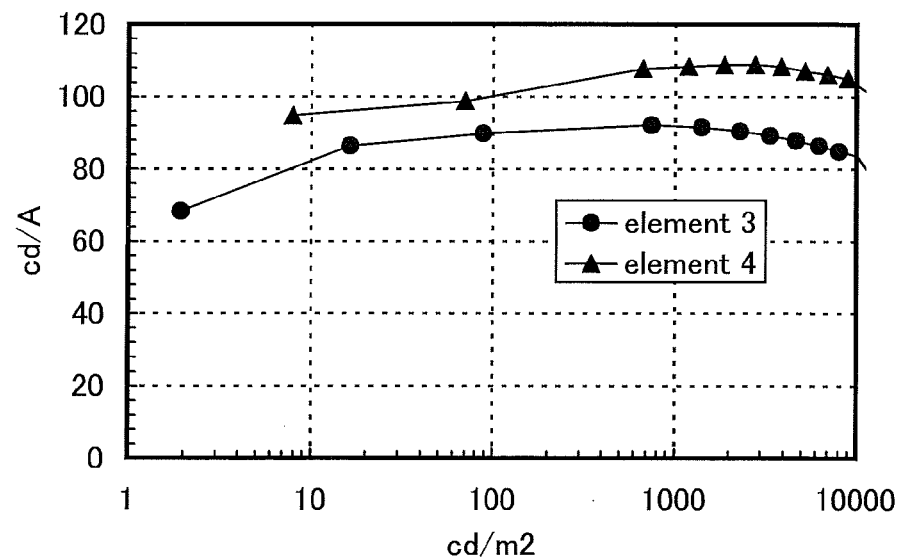
FIG. 26 shows luminance-current efficiency characteristics of a light-emitting element 3 and a light-emitting element 4.
Figure 27:
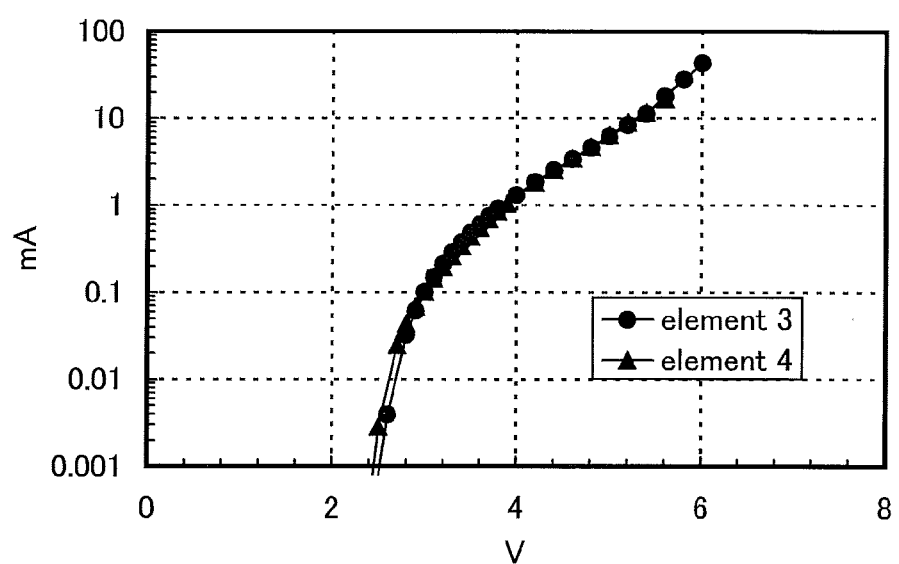
FIG. 27 shows voltage-current characteristics of a light-emitting element 3 and a light-emitting element 4.

FIG. 24 shows current density-luminance characteristics of the light-emitting elements 3 and 4, FIG. 25 shows voltage-luminance characteristics thereof, FIG. 26 shows luminance-current efficiency characteristics thereof, and FIG. 27 shows voltage-current characteristics thereof.

FIG. 26 reveals that the light-emitting element 3 and the light-emitting element 4, which use the heterocyclic compounds of embodiments of the present invention in the light-emitting layers and the electron-transport layers, have reduced power consumption and high efficiency.

Table 4 shows initial values of main characteristics of the light-emitting elements 3 and 4 at a luminance of about 1000 cd/m$^2$.

TABLE 4

|  | Voltage (V) | Current (mA) | Current Density (mA/cm$^2$) | Chromaticity (x, y) | Luminance (cd/m$^2$) | Current Efficiency (cd/A) | Power Efficiency (lm/W) | External Quantum Efficiency (%) |
|---|---|---|---|---|---|---|---|---|
| Light-emitting Element 3 | 2.8 | 0.032 | 0.81 | (0.41, 0.58) | 740 | 92 | 100 | 24 |
| Light-emitting Element 4 | 2.8 | 0.043 | 1.1 | (0.39, 0.60) | 1200 | 110 | 120 | 28 |

The above results in Table 4 also show that the light-emitting elements 3 and 4 fabricated in this example have high luminance and high current efficiency.

Figure 28:
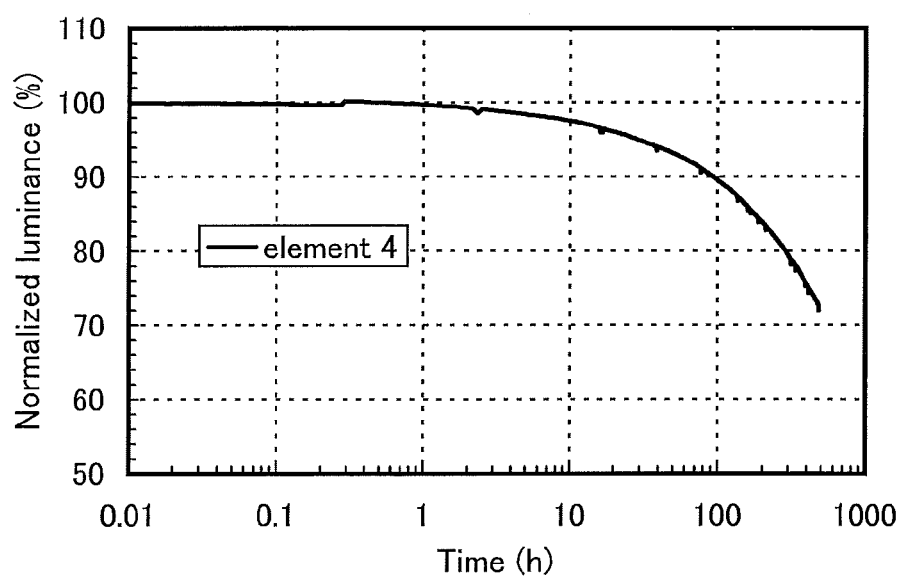
FIG. 28 shows reliability of a light-emitting element 4.

The light-emitting element 4 was subjected to a reliability test. FIG. 28 shows results of the reliability test. In FIG. 28, the vertical axis indicates normalized luminance (%) with an initial luminance of 100% and the horizontal axis indicates driving time (h) of the element. Note that in the reliability test, the light-emitting element 4 was driven under the conditions where the initial luminance was set to 5000 cd/m$^2$ and the current density was constant. The light-emitting element 4 kept about 83% of the initial luminance after 100 hours elapsed.

TABLE 3

|  | First electrode | Hole-injection Layer | Hole-transport Layer | Light-emitting Layer | | | Electron-transport Layer | Electron-injection Layer | Second Electrode |
|---|---|---|---|---|---|---|---|---|---|
| Light-emitting Element 3 | ITSO (110 nm) | DBT3P-II: MoO$_x$ (4:2 40 nm) | BPAFLP (20 nm) | * | ** | | 6Ph-4mDBTBPPm-II (15 nm) | Bphen (15 nm) | LiF (1 nm) | Al (200 nm) |
| Light-emitting Element 4 | ITSO (110 nm) | DBT3P-II: MoO$_x$ (4:2 40 nm) | BPAFLP (20 nm) | *** | **** | | 6FL-4mDBTBPPm (15 nm) | Bphen (10 nm) | LiF (1 nm) | Al (200 nm) |

* 6Ph-4mDBTBPPm-II:PCBBiF:[Ir(tBuppm)$_2$(acac)] (0.7:0.3:0.05 20 nm)
** 6Ph-4mDBTBPPm-II:PCBBiF:[Ir(tBuppm)$_2$(acac)] (0.8:0.2:0.05 20 nm)
*** 6FL-4mDBTBPPm:PCBBiF:[Ir(tBuppm)$_2$(acac)] (0.7:0.3:0.05 20 nm)
**** 6FL-4mDBTBPPm:PCBBiF:[Ir(tBuppm)$_2$(acac)] (0.8:0.2:0.05 20 nm)

Further, the fabricated light-emitting elements 3 and 4 were sealed in a glove box containing a nitrogen atmosphere so as not to be exposed to the air (specifically, a sealant was applied onto an outer edge of the element and heat treatment was performed at 80° C. for 1 hour at the time of sealing).

The results of the reliability test showed that the light-emitting element 4 has high reliability. In addition, it was confirmed that with the use of the heterocyclic compound that is one embodiment of the present invention, a light-emitting element with a long lifetime can be obtained.

This application is based on Japanese Patent Application serial no. 2012-172801 filed with Japan Patent Office on Aug. 3, 2012, the entire contents of which are hereby incorporated by reference.

What is claimed is:

1. A light-emitting element comprising an organic compound represented by a formula (G1):

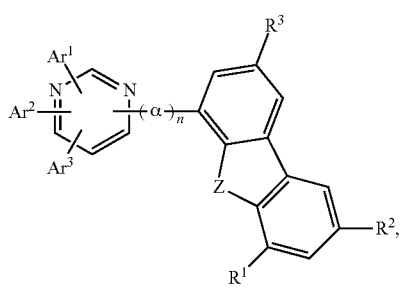

(G1)

wherein $Ar^1$ to $Ar^3$ separately represent hydrogen, an alkyl group having 1 to 4 carbon atoms, a substituted or unsubstituted phenyl group, or a substituted or unsubstituted biphenyl group, wherein $R^1$ to $R^3$ separately represent hydrogen, an alkyl group having 1 to 4 carbon atoms, or a substituted or unsubstituted aryl group having 6 to 13 carbon atoms, wherein α represents a substituted or unsubstituted phenylene group, wherein n is 2 or 3, wherein Z represents oxygen or sulfur, wherein the light-emitting element further comprises a layer between a pair of electrodes, the layer comprising:
  the organic compound;
  an aromatic amine; and
  a phosphorescent compound, and wherein a combination of the organic compound and the aromatic amine is configured to form an exciplex.

2. The light-emitting element according to claim 1, wherein the organic compound is represented by a formula (G2):

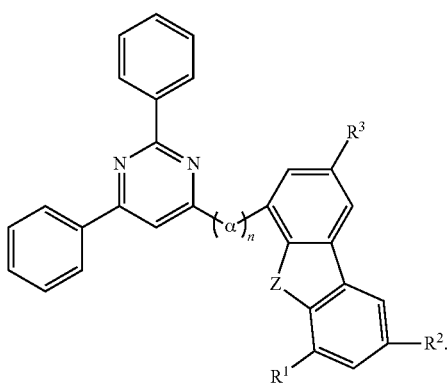

(G2)

3. The light-emitting element according to claim 1, wherein the organic compound is represented by a formula (100):

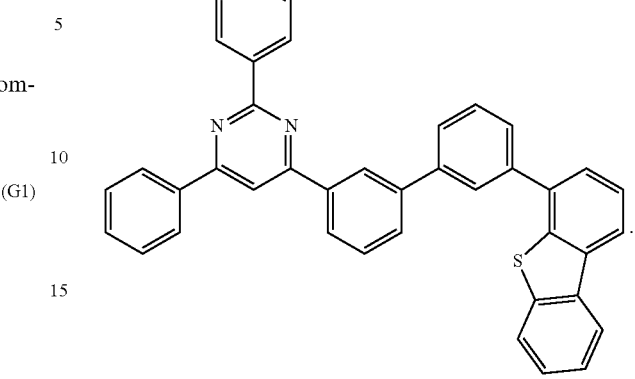

(100)

4. The light-emitting element according to claim 1, wherein the organic compound is represented by a formula (101):

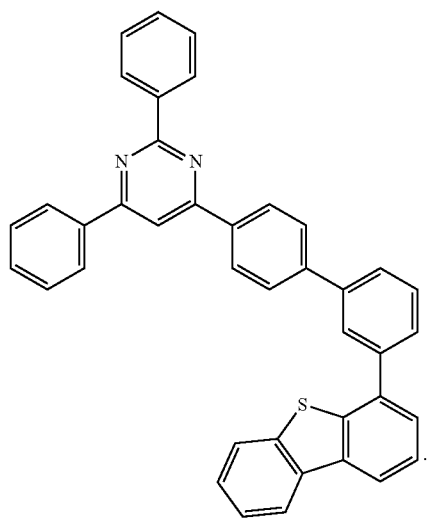

(101)

5. The light-emitting element according to claim 1, further comprising an electron-transport layer between the layer and one of the pair of electrodes, wherein the electron-transport layer comprises the organic compound.

6. A light-emitting device comprising the light-emitting element according to claim 1.

7. An electronic device comprising the light-emitting device according to claim 6.

8. A lighting device comprising the light-emitting device according to claim 6.

9. A light-emitting element comprising:
  a layer between a pair of electrodes, the layer comprising:
    an organic compound comprising a pyrimidine ring;
    an aromatic amine; and
    a phosphorescent compound,
  wherein a combination of the organic compound and the aromatic amine is configured to form an exciplex.

10. The light-emitting element according to claim 9, wherein the organic compound further comprises a ring including a hole-transport skeleton.

11. The light-emitting element according to claim 9, wherein the organic compound has a molecular weight greater than or equal to 400 and less than or equal to 1200.

12. The light-emitting element according to claim 10, wherein the ring including the hole-transport skeleton is a carbazole ring, a dibenzothiophene ring, or a dibenzofuran ring.

13. The light-emitting element according to claim 9, wherein the aromatic amine comprises a pyrimidine skeleton.

14. A light-emitting device comprising the light-emitting element according to claim 9.

15. An electronic device comprising the light-emitting device according to claim 14.

16. A lighting device comprising the light-emitting device according to claim 14.

* * * * *